(12) United States Patent
Bokelman et al.

(10) Patent No.: US 9,757,527 B2
(45) Date of Patent: Sep. 12, 2017

(54) RETRACTABLE NEEDLE ADAPTERS AND SAFETY SYRINGES

(71) Applicant: UNL Holdings LLC, New York, NY (US)

(72) Inventors: Kevin L. Bokelman, San Diego, CA (US); Eduardo Ho, Carlsbad, CA (US); Robert Scott Russo, Malvern, PA (US); Brandon J. McKee, Nesquehoning, PA (US); John W. Carosi, Collegeville, PA (US); Christian P. Brandt, York, PA (US); Jyoti Gupta, Atlanta, GA (US); Ramin Mojdehbakhsh, Mechanicsburg, PA (US)

(73) Assignee: UNL Holdings LLC, New York, NY (US)

( * ) Notice: Subject to any disclaimer, the term of this patent is extended or adjusted under 35 U.S.C. 154(b) by 135 days.

(21) Appl. No.: 14/635,376

(22) Filed: Mar. 2, 2015

(65) Prior Publication Data

US 2015/0174339 A1 Jun. 25, 2015

Related U.S. Application Data

(63) Continuation of application No. 14/207,037, filed on Mar. 12, 2014, now Pat. No. 8,979,795, and a
(Continued)

(51) Int. Cl.
*A61M 5/32* (2006.01)
*A61M 5/34* (2006.01)

(52) U.S. Cl.
CPC .......... *A61M 5/3221* (2013.01); *A61M 5/321* (2013.01); *A61M 5/3234* (2013.01);
(Continued)

(58) Field of Classification Search
CPC ...... A61M 5/3221; A61M 5/34; A61M 5/321; A61M 2207/00
See application file for complete search history.

(56) References Cited

U.S. PATENT DOCUMENTS

| | | | |
|---|---|---|---|
| 6,673,044 B2 | 1/2004 | Righi et al. | |
| 2003/0093038 A1 | 5/2003 | Chiang | |
| 2008/0021389 A1 | 1/2008 | Runfola | |

FOREIGN PATENT DOCUMENTS

| | | |
|---|---|---|
| JP | 2004-500177 A | 1/2004 |
| WO | WO 93/12830 A1 | 7/1993 |

(Continued)

OTHER PUBLICATIONS

European Patent Office, International Search Report in International Application No. PCT/US2014/024781, 5 pages (May 21, 2014).
(Continued)

*Primary Examiner* — Bradley Osinski
(74) *Attorney, Agent, or Firm* — Hamilton, Brook, Smith & Reynolds, P.C.

(57) ABSTRACT

Barrel adapters for safety syringes include a barrel and a plunger assembly adapted to move within the barrel, a barrel tip adapted to be sealingly engaged with a distal end of the barrel and a needle retraction mechanism barrel having a needle subassembly and an actuator subassembly. The needle subassembly includes a needle, and a needle-over-mold (NOM) through which the needle extends. The needle subassembly is disposed at least partially within the barrel tip, and adapted to move from an injection position in which the needle extends from a distal end of the barrel tip to a retracted position in which the needle is disposed within at least one of the barrel tip or the barrel. The actuator subassembly includes a needle seal, a push-bar, and an actuator surface. The needle retraction mechanism barrel
(Continued)

includes a biasing member and an actuable locking arrangement. A syringe includes such barrel adapters.

10 Claims, 21 Drawing Sheets

Related U.S. Application Data continuation of application No. PCT/US2014/024781, filed on Mar. 12, 2014.

(60) Provisional application No. 61/777,362, filed on Mar. 12, 2013.

(52) U.S. Cl.
CPC ....... *A61M 5/34* (2013.01); *A61M 2005/3236* (2013.01); *A61M 2207/00* (2013.01); *Y10T 29/4984* (2015.01)

(56) References Cited

FOREIGN PATENT DOCUMENTS

| | | |
|---|---|---|
| WO | WO 2008/111931 A1 | 9/2008 |
| WO | WO 2013/126853 A2 | 8/2013 |

OTHER PUBLICATIONS

European Patent Office, Written Opinion of the International Searching Authority in International Application No. PCT/US2014/024781, 5 pages (May 21, 2014).

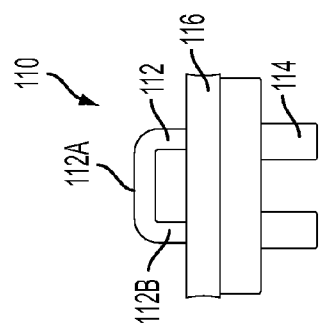
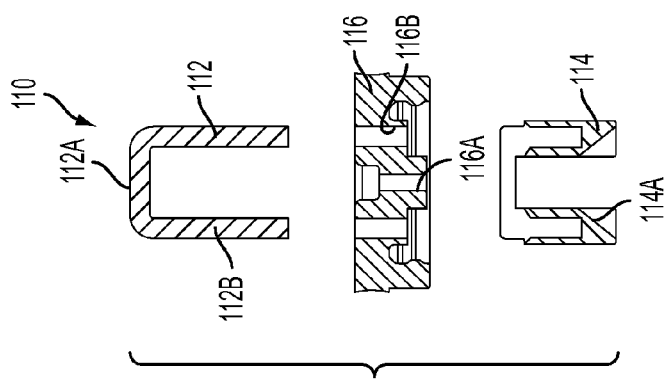
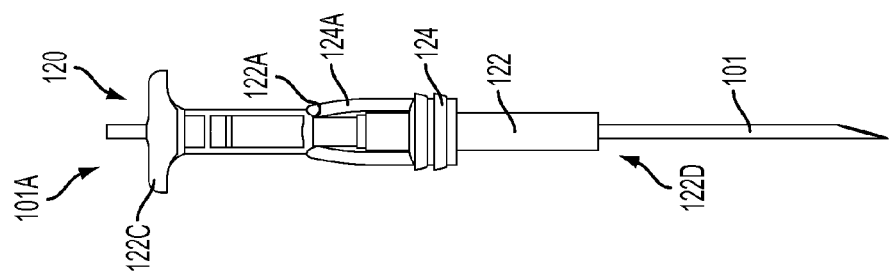
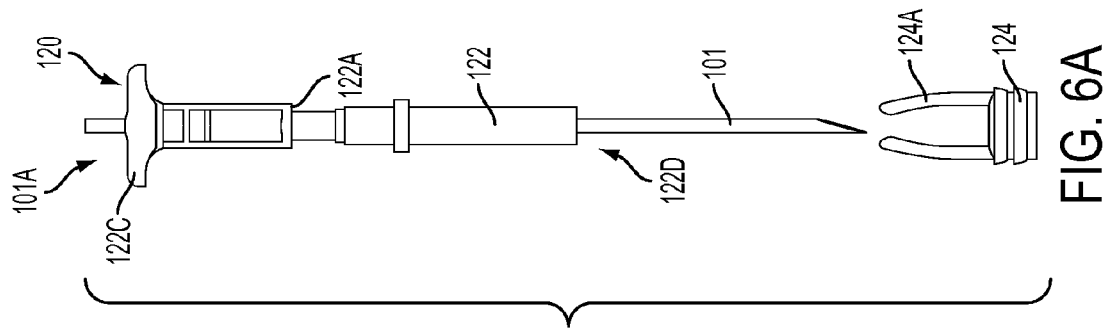

RETRACTABLE NEEDLE ADAPTERS AND SAFETY SYRINGES

CROSS-REFERENCE TO RELATED APPLICATIONS

This application is a continuation of U.S. application Ser. No. 14/207,037 and International Patent Application No. PCT/US2014/024781, both filed Mar. 12, 2014, which claim priority to U.S. Provisional Application No. 61/777,362 filed on Mar. 12, 2013, all of which are included by reference herein in their entirety for all purposes.

FIELD OF THE INVENTION

The present invention relates to safety syringes. More specifically, the embodiments of the present invention relate to barrel-adaptable needle retraction systems, syringes which integrate such safety mechanisms, methods for manufacturing such safety syringes, and their methods of use.

BACKGROUND OF THE INVENTION

Manually activated pre-filled syringe cartridges are commercially available from a variety of manufacturers, including the owner and assignee of the present invention. Pre-filled syringe cartridges are used in the administration of drug solutions, drug suspensions, vaccines, medicinal therapies, and any other liquid medicament by parenteral injection.

As such, pre-filled syringe cartridges include a primary drug chamber, a hypodermic needle permanently affixed to and in fluid communication with the drug chamber, and a piston slidably received in the drug chamber. The pistons of the pre-filled syringe cartridges often include a plunger subassembly, which may include a plunger inner and a plunger outer, to force the liquid medicament from the needle. Pre-filled syringes are typically prepared by pharmaceutical companies or sterile filling contractors in a sterile filling room in which the drug and the syringe are brought together in a sterile manufacturing environment wherein all components and drug solutions are isolated from microbial contamination.

The practice of sharing syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers.

Furthermore, health professionals may be exposed to used syringes, which can lead to inadvertent needlestick injuries and possible exposure to infective pathogens or other contaminants. In response to this problem, retractable syringes have been developed with the aim of preventing syringe re-use and/or needlestick injury by used syringes.

In developing such retractable syringes, relatively complicated retractable needle assemblies have been devised which often are developed for a particular syringe barrel shape or configuration and cannot be readily mounted to a syringe barrel having a different shape or configuration. This is particularly a problem with glass syringe barrels, which are generally in short supply, many of which glass barrels do not have a desired shape or configuration for mounting a retractable needle subassembly. Accordingly, many existing safety syringes require specifically-tailored retraction mechanisms and barrel configurations, which may require complex manufacturing processes or operational changes.

The materials employed in the manufacture of such safety syringes must meet complex criteria for regulatory approval. Additionally, safety syringes must remain aesthetically-similar to conventional syringes to facilitate broad adoption and must be easy-to-use for self-administering patients.

BRIEF SUMMARY OF THE INVENTION

Embodiments of the present invention relate to barrel-adaptable needle retraction systems, syringes which integrate such safety mechanisms, methods of manufacturing such safety syringes, and their methods of use. Embodiments of the present invention provide reliable needle retraction, for improved user safety, without requiring complex manufacturing processes or operational changes for pharmaceutical companies or contract drug fillers. Additionally, embodiments of the present invention provide configurations which utilize materials and components which are readily employable for pharmaceutical use, many of which are increasingly considered off-the-shelf or standard components. Furthermore, the present invention provides components and devices which are aesthetically-similar to conventional syringes, which do not have needle retraction mechanisms, are ergonomically attractive to end-users, such as a medical practitioners and self-administering patients, and provide highly desired integrated safety features. The novel barrel adapters of the present invention are notably able to be adapted to primary drug barrels of varying configurations and materials such as, preferably, straight-barrel glass barrels to provide integrated needle assemblies and retraction mechanisms to the barrel. Such embodiments may be utilized for pre-filled or fill at time-of-use injectable drug syringes. As such, the adaptable retraction mechanisms of the present invention may be flexibly attached, affixed, mounted, or otherwise mated to standard barrels, such as straight-glass barrels. These embodiments, accordingly, provide novel and cost-efficient components and devices which are readily integrated into drug filling processes.

In an aspect of embodiments of the invention, there is provided a barrel adapter for a safety syringe having a barrel and a plunger assembly adapted to move within the barrel. The barrel adapter includes a barrel tip adapted to be sealingly engaged with a distal end of the barrel and a needle retraction mechanism having a needle subassembly and an actuator subassembly. The needle subassembly includes a needle, a needle-over-mold (NOM) through which the needle extends, and a retention mechanism. The needle subassembly is disposed at least partially within the barrel tip, and adapted to move from an injection position in which the needle extends from a distal end of the barrel tip to a retracted position in which the needle is disposed within at least one of the barrel tip or the barrel. The actuator subassembly includes a needle seal, a push-bar, and an actuating surface. The needle retraction mechanism includes a biasing member and an actuable locking arrangement. The locking arrangement is disposed to maintain the biasing member in an energized position when the locking arrangement is locked and release the biasing member when actuated. The locking arrangement is actuable by depression of the plunger assembly, the plunger seal exerting a force on the push bar to move the actuating surface in an axial direction to actuate the retraction mechanism. The biasing member is disposed to move the needle from the injection position to the refracted position when the biasing member is released from the energized position.

In a further aspect of embodiments of the invention, there is provided an automatically retractable safety syringe including a barrel having a distal end and a proximal end, a plunger assembly adapted to move within the barrel, and a barrel adapter sealingly engaged with the distal end of the barrel. The safety syringe further includes a plunger assembly adapted to move within the barrel, the plunger assembly including a plunger rod and a plunger seal. The barrel adapter includes a barrel tip adapted to be sealingly engaged with a distal end of the barrel and a needle retraction mechanism having a needle subassembly and an actuator subassembly. The needle subassembly includes a needle, a needle-over-mold (NOM) through which the needle extends, and a retention mechanism. The needle subassembly is disposed at least partially within the barrel tip, and adapted to move from an injection position in which the needle extends from a distal end of the barrel tip to a retracted position in which the needle is disposed within at least one of the barrel tip or the barrel. The actuator subassembly includes a needle seal, a push-bar, and an actuating surface. The needle retraction mechanism includes a biasing member and an actuable locking arrangement. The locking arrangement is disposed to maintain the biasing member in an energized position when the locking arrangement is locked and release the biasing member when actuated. The locking arrangement is actuable by depression of the plunger assembly, continued movement of the plunger seal of which moves the actuating surface in an axial direction to actuate the actuable locking mechanism to retract the needle. The biasing member is disposed to move the needle from the injection position to the retracted position when the biasing member is released from the energized position. A flange may be included in at least one embodiment of the syringe to, for example to close off the proximal end of the syringe and barrel from the outside environment and/or to provide a tangible aspect for ergonomic gripping of the syringe.

In another aspect of embodiments of the invention, there is provided a method of assembling an automatically retractable safety syringe. The method includes the steps of disposing a plunger assembly to move within a barrel, sealingly engaging a barrel tip with a distal end of the barrel, disposing a needle subassembly for movement within the barrel tip and the barrel between an injection position wherein a needle of the needle subassembly extends from the barrel tip and a retracted position wherein the needle is disposed within at least one of the barrel tip or the barrel, and disposing a needle retraction mechanism including a biasing member and an actuable locking arrangement within the barrel. The locking arrangement is disposed to maintain the biasing member in an energized position when the locking arrangement is locked and release the biasing member when actuated. The locking arrangement is actuable by depression of the plunger assembly, the biasing member being disposed to move the needle from the injection position to the retracted position when the biasing member is released from the energized position.

Accordingly, the barrel adapters include the components necessary for needle retention and retraction, and are configured to mate with standard barrels. The barrel adapter is configured to mate and be affixed, through a number of known methods, to the distal end of a barrel. In at least one embodiment, the barrel adapters are configured to mate with barrels that are substantially straight in cross-sectional profile (e.g., substantially parallel along at least a distal portion of the barrel), such as glass straight-barrels. The barrel adapters may be configured to mate with the barrel in a number of different ways. In a preferred embodiment, however, the barrel adapters are configured such that at least a proximal connecting portion is shaped to be mounted to and reside within the inner diameter of a distal portion of the barrel. As such, the barrel adapter may be connected to a standard straight-barrel drug chamber by being inserted into and attached, affixed, mounted, or otherwise mated to the distal end of the barrel. This enables the barrel adapters to be flexibly adaptable to barrels of all types, particularly standard glass straight-barrels, thereby providing potential manufacturing advantages and operational cost-savings. The barrel adapters of the present invention, therefore, simplify the assembly of needle refraction mechanisms with standard barrels to produce syringes with integrated needle safety features. In any of these embodiments of the barrel adapter, the biasing member is mounted, either fixedly or movably, generally within the barrel tip. The biasing member is biased to expand in the proximal direction and substantially along the longitudinal axis of the barrel.

The barrel adapters of the present invention enable selection and adaptation of varying needle assemblies with standard barrels. In other words, the design and configuration of the present invention allows a user to select a needle and/or needle subassembly of a particular design or dimensions and adapt it to a syringe barrel for drug delivery. Accordingly, the barrel adapters of the present invention enable further customization of the drug delivery device by the user, allowing them to employ the integrated refraction mechanism of the barrel adapter to any barrel to produce a safety syringe. For example, the barrel adapters and needle assemblies may be configured to provide a number of different needle lengths. The user may then select the barrel adapter with their desired needle length and adapt it to a syringe to deliver the drug. This flexibility of the present invention is particularly useful for drug delivery that is subcutaneous or intramuscular. The barrel adapters of the present invention may be configured to enable such flexibility. One or more additional components may be utilized to provide this adaptive feature. For example, one or more connecting components may be utilized to connect the barrel tip of the barrel adapter to the barrel. In one such embodiment, one connecting component (such as a receiving component) may be fixedly mounted on a distal end of a glass barrel. The receiving component may directly receive and engage the barrel tip with the integrated retraction mechanism. Alternatively, the barrel adapter may include one or more additional connecting components (such as a mating component) which are used to engage the receiving component. Other optional components, such as elastomeric seals, which are known to one having ordinary skill in the art, may be necessary and incorporated into the device to facilitate the connection between the barrel adapter and the barrel.

Additionally, the barrel adapters of the present invention utilize materials that are substantially non-reactive with therapeutic fluids or drugs, and are suitable for use in pharmaceutical grade applications. The novel barrel adapters are configured to minimize or eliminate the possibility of contact or interaction between degradable materials, such as certain plastics, with the therapeutic fluids or drugs. The barrel adapters, with adaptable needle retention and retraction mechanisms, also provide fluid pathways from the primary drug chamber to the patient, through the needle, which are substantially absent of degradable materials. Such novel adapter configurations, when integrated into barrels to provide the novel safety syringes of the present invention, provide increased stability and shelf-life parameters to the drug and drug delivery devices. These characteristics are thought to be highly desirable for generally all pharmaceutical treatments, but may be of particular advantage in syringes for use with biologics and other complex therapies.

In one embodiment, for example, a metal needle is retained within a glass barrel by an elastomeric needle seal at a proximal end of the needle and by an aperture of a plastic barrel tip at a portion of the needle that is distal to the needle seal, such that the drug fluid pathway contains (and the drug contacts) only glass, elastomer, and metal. In this way, the drug travels from drug chamber to patient without contacting any plastic. In other embodiments, other material combinations or fewer materials may be utilized for the drug fluid pathway. Embodiments of the present invention also substantially reduce the number of components necessary for integrated needle retention and retraction mechanisms. Elimination of such components can further reduce the possibility of drug interaction with degradable materials, while also providing potential manufacturing advantages and operational cost-savings. The reduction of components in some embodiments of the present invention can be achieved by utilizing certain components for multiple functions.

In another embodiment, the present invention provides a safety syringe that includes a barrel, a plunger assembly, and a barrel adapter. The barrel adapter includes a barrel tip, a biasing member, a locking mechanism, and a needle subassembly. The needle subassembly may generally include a needle, a needle hub, and a needle seal. The needle is configured to pass-through the needle subassembly, locking mechanism, biasing member, and barrel tip such that, one end the needle is within the barrel and another end the needle passes through an aperture in the barrel tip. The barrel may be substantially cylindrical, having along its longitudinal axis a distal end for drug injection, a proximal end for injection control, and at least a portion of the barrel interior for drug containment. The barrel adapter is configured to mate and be affixed, through a number of known methods, to the distal end of a barrel. The barrel adapter is capable of coupling or mounting to, or engaging with, a barrel of the safety syringe. In any of these embodiments of the barrel adapter, the biasing member is mounted, either fixedly or movably, generally within the barrel tip and the distal end of the barrel. The biasing member is biased to expand in the proximal direction and substantially along the longitudinal axis of the barrel. The plunger assembly may include a plunger rod and a plunger stopper or seal. The plunger rod may be connected to the plunger seal by a number of different connections such as, for example, being screwed into the plunger seal. The plunger assembly may be mounted at the proximal end of the barrel while the barrel adapter is mounted at the distal end of the barrel. The plunger seal may comprise an elastomeric material and be sized such that it provides a compression fit with an inner diameter of the barrel such that it maintains a sterile drug chamber with container integrity. The plunger seal may also include an aperture, such as an axial pass-through, for example to enable removal of air from the drug chamber as the plunger seal is depressed into position within the barrel. The plunger seal aperture may be closed or capped by connection with the plunger rod, which may be screwed into the plunger seal aperture.

One or more embodiments of the present invention may optionally include certain standard components. For example, the barrel adapter configurations and syringe devices of the present invention may include one or more O-rings. In at least one embodiment, one or more O-rings are employed to seal the barrel tip within the barrel and/or to ensure a sterile environment and container integrity within the drug chamber of the barrel. Additionally or alternatively, the barrel adapter may include one or more controlling members to facilitate the control of the rate of retraction. Similarly, the barrel adapter may include one or more needle blocking mechanisms, such as clips, flaps, flanges, or the like, which function to prevent the needle from being translated or protruding out of the barrel through the aperture of the barrel tip after the retraction mechanism has been initiated or completed. Furthermore, the safety syringe may include one or more components for aesthetics, ease-of-use, or other purposes. For example, one or more embodiments of the present invention may include a finger flange.

The novel barrel adapter designs of the present invention obviate the need to have a particular barrel shape or configuration for mounting a needle subassembly thereto. Another desirable feature of the present invention is to provide a relatively simplified needle subassembly which comprises fewer components, thereby providing a user-friendly and safe retractable syringe while keeping manufacturing costs to a minimum and/or facilitating mass distribution of retractable syringes. Embodiments of the present invention also provide configurations that allow the use of standard, commercially-available components, which may reduce overall manufacturing costs, streamline assembly processes, and avoid regulatory concerns often associated with non-standard materials and components. Additionally, the invention provides efficient delivery of fluid contents, thereby minimizing wastage of fluid contents, and/or integrates one or more locking systems to prevent or at least minimize syringe re-use and/or needle stick injury.

Accordingly, in yet another embodiment the present invention provides a method for assembling a safety syringe having a barrel adapter, a plunger assembly, and a barrel having a longitudinal axis. The method includes the steps of: assembling the barrel adapter which includes a barrel tip, a biasing member, a locking mechanism, and a needle subassembly; mounting the barrel tip to a distal end of the barrel; and mounting the plunger assembly having a plunger seal and a plunger rod to a proximal end of the barrel. The barrel adapter may be fixedly affixed, such as by glue, to the distal end of the barrel. The plunger assembly may be movably mounted to the distal end of the barrel by first inserting the plunger seal into the barrel and then inserting the plunger rod into the plunger seal by screw connection or another known method of connection. The method for assembling the safety syringe may further include the step of filling the barrel with a drug, after the step of mounting the barrel tip, but prior to the step of mounting the plunger assembly. In at least one embodiment, the barrel adapter is in a compressed configuration prior to mounting into the barrel. For example, the biasing member may be compressively engaged, such as in an energized stage, between the locking mechanism and the barrel tip prior to mounting the barrel adapter into the barrel. In another embodiment, these components may be mounted into the barrel prior to compressing and locking the biasing member into place. Accordingly, the method may further include the steps of compressing the biasing member and locking the locking mechanism into an engaged and energized position after the mounting of the barrel adapter to the barrel. It is contemplated that the plunger assembly may be utilized to compress the biasing member and lock the locking mechanism in some embodiments. In some embodiments, such as in a prefilled safety syringe configuration, at least part of the plunger assembly may then be removed to facilitate the filling process. For example, the plunger rod may be removed but the plunger seal may be retained in the barrel for the filling process. In other embodiments, such as in a fill-at-time-of-use configuration, the plunger assembly may be retained in the barrel of the safety syringe and drawn in the proximal direction to facilitate the filling of the barrel through the barrel adapter and, specifically, the needle subassembly. As would be appreciated by an ordinarily skilled artisan, the drug may be a solution, a powder, a suspension, or the like, or any combination thereof.

In another embodiment the present invention provides a method of manufacturing a safety syringe which includes the steps of: mounting a retraction mechanism which includes a biasing member, a locking mechanism, and a needle subassembly through a proximal end of a barrel, wherein a distal end of the retraction mechanism is axially translated to reside substantially within the barrel tip; and mounting the plunger assembly having a plunger seal and a plunger rod to a proximal end of the barrel. The plunger assembly may be movably mounted to the distal end of the barrel by first inserting the plunger seal into the barrel and then inserting the plunger rod into the plunger seal by screw connection or another known method of connection. The method for manufacturing the safety syringe may further include the step of filling the barrel with a drug, after the step of mounting the retraction mechanism but prior to the step of mounting the plunger assembly. The plunger seal may be mounted prior to, or in connection with, the plunger rod. In at least one embodiment, the retraction mechanism is in a compressed configuration prior to mounting into the barrel. For example, the biasing member may be compressively engaged, such as in an energized stage, prior to mounting the retraction mechanism into the barrel. In another embodiment, these components may be mounted into the barrel prior to compressing and locking the biasing member into place. In one such embodiment, the barrel tip is mounted to the distal end of the barrel while the remainder of the barrel adapter components are inserted through a proximal end of the barrel, axially translated within the barrel to the distal end of the barrel, and therein compressed and engaged to the barrel tip in an energized position. Accordingly, the method may further include the steps of compressing the biasing member and locking the locking mechanism into an engaged and energized position after the mounting of the retraction mechanism into the barrel.

A drug or pharmaceutical treatment may be filled in a portion of the barrel between the proximal end and the distal end constituting a drug chamber. The barrel adapter and the plunger assembly may be connected to the barrel by a number of known methods. For example, the barrel adapter may be fixedly attached, by a glue or other known method of adhesion or connection such as compression fit, to the distal end of the barrel. The syringe barrel may then be filled with a desired quantity of drug at the proximal end of the barrel. After completion of the filling, the plunger assembly may be mounted at the proximal end of the syringe barrel. As would be appreciated by one having ordinary skill in the art, this filling and assembly process may be completed under vacuum and/or a sterile environment to facilitate the aseptic manufacturing of the safety syringe. These safety syringes are configured such that they may readily be manufactured individually, or in a group, as is the case in a tray-based filling process.

In another embodiment, the present invention relates to a method of use for a safety syringe having a barrel adapter, a plunger assembly, and a barrel having a longitudinal axis. The barrel adapter, which may be mounted to a distal end of the barrel, includes a barrel tip, a biasing member such as a compression spring, a locking mechanism, and a needle subassembly; wherein the components of the barrel adapter reside substantially within the barrel tip and the distal end of the barrel. The plunger assembly, which may be mounted to a proximal end of the barrel, includes a plunger seal and a plunger rod. The barrel adapter may be fixedly affixed, such as by glue, to the distal end of the barrel. The plunger assembly may be movably mounted to the distal end of the barrel by first inserting the plunger seal into the barrel and then inserting the plunger rod into the plunger seal by screw connection or another known method of connection. A drug may be contained within a portion of the barrel referred to as a drug chamber. The drug may be prefilled into the barrel during the manufacturing and filling process or filled at time-of-use or just prior to time-of-use. The method of use includes the steps: depressing the plunger assembly to facilitate delivery of a drug from the barrel; upon completion of the drug delivery, triggering the locking mechanism to release the biasing member from its energized state; and, by contact between the biasing member and the needle subassembly, causing the needle subassembly to retract into the barrel. In at least one embodiment, the locking mechanism may include an interface on the barrel tip which engages the locking mechanism. Upon activation by the user, the needle hub may be employed to initiate the release of the locking mechanism from its engagement with the barrel tip. By releasing the locking mechanism from the barrel tip, the biasing member is allowed to expand causing the needle subassembly to retract in the proximal direction substantially along a longitudinal axis of the barrel. In some embodiments of the present invention, the entire needle subassembly is caused to retract, while in other embodiments only certain components thereof, including the needle, are caused to retract upon release of the locking mechanism and activation of the biasing member. Similarly, in some embodiments of the present invention, the locking mechanism is caused to retract with the needle subassembly while in other embodiments the locking mechanism remains substantially stationary but enables the needle subassembly, or components thereof, to move.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, embodiments of the present invention may include one or more additional components which may be considered standard components in the industry of medical devices. The components, and embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 6A is an enlarged exploded view of the needle subassembly component of the barrel adapter according to an embodiment of FIG. 1;

FIG. 6B is an enlarged assembled view of the needle subassembly component shown in FIG. 6A;

FIG. 7A is an enlarged exploded view of the actuator subassembly component of the barrel adapter according to the embodiment of FIG. 1;

FIG. 7B is an enlarged assembled view of the actuator subassembly component shown in FIG. 7A;

DETAILED DESCRIPTION OF THE INVENTION

Figure 1:
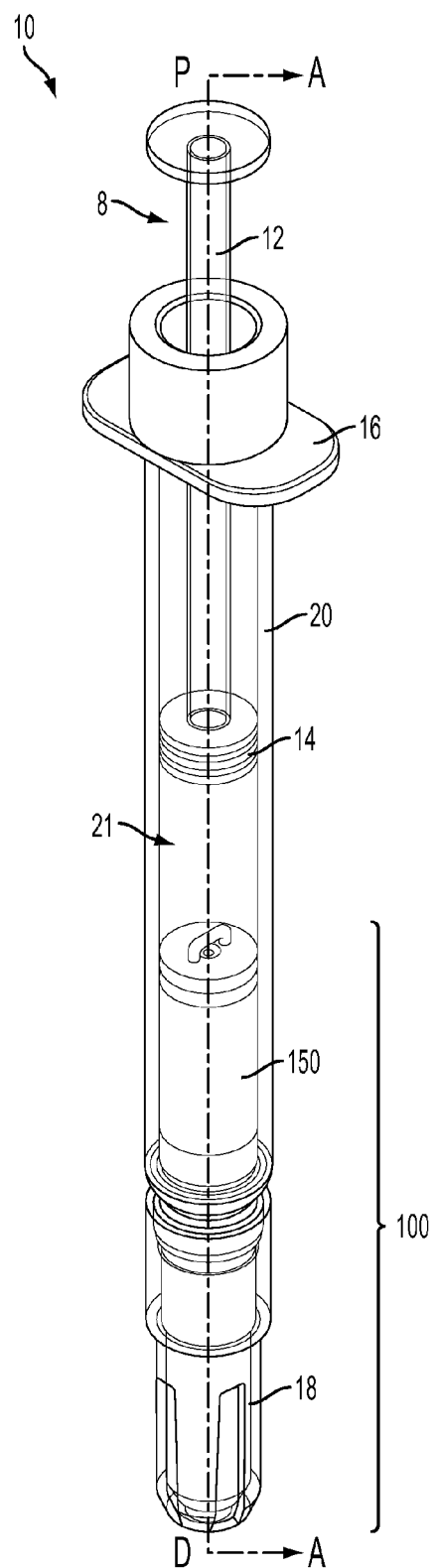
FIG. 1 is an isometric view of a first embodiment of a safety syringe according to teachings of the present invention.

The embodiments of the present invention provide reliable needle retraction, for improved user safety, without requiring complex manufacturing processes or operational changes for pharmaceutical companies or contract drug fillers. The embodiments of the present invention provide for a relatively simplified needle subassembly which comprises fewer components, thereby providing a user-friendly and safe retractable syringe while keeping manufacturing costs to a minimum and/or facilitating mass distribution of retractable syringes. The novel barrel adapters of the present invention are notably able to be adapted to primary drug barrels of varying configurations and materials such as, preferably, straight-barrel glass barrels to provide integrated needle assemblies and retraction mechanisms to the barrel. Such embodiments may be utilized for pre-filled or fill at time-of-use injectable drug syringes. As such, the adaptable retraction mechanisms of the present invention may be flexibly attached, affixed, mounted, or otherwise mated to standard barrels, such as straight-glass barrels. The barrel adapters may be configured to mate with the barrel in a number of different ways, however, in a preferred embodiment, the barrel adapters are configured such that at least a proximal connecting portion is shaped to be mounted to, and reside within, the inner diameter of a distal portion of the barrel. As such, the barrel adapter may be connected to a standard straight-barrel drug chamber by having at least a proximal portion of the adapter inserted into and attached, affixed, mounted, or otherwise mated to the distal end of the barrel. The novel barrel adapter designs of the present invention therefore obviate the need to have a particular barrel shape or configuration for mounting a needle subassembly thereto. This may substantially reduce manufacturing costs, especially those associated with the manufacture of specifically tailored glass barrels. The novel barrel adapters of the present invention can be mounted to, for example, straight glass barrels thereby simplifying the manufacturing process and costs associated with the manufacture of more complex barrel shapes.

The barrel adapters of the present invention may be selectable at the time of use or pre-attached to the barrel during manufacturing. In the selectable option, the design and configuration of the present invention allows a user to select a needle and/or needle subassembly of a particular design or dimensions and adapt it to a syringe barrel for drug delivery. For example, the barrel adapters and needle assemblies may be configured to provide a number of different needle lengths or thicknesses. The user may then select the barrel adapter with their desired needle dimensions and adapt it to a syringe to deliver the drug. In the embodiments shown in FIG. 1, the barrel adapter is directly mounted to the barrel. One or more additional components may be utilized to provide this adaptive feature. For example, one or more connecting components may be utilized to connect the barrel tip of the barrel adapter to the barrel. In one such embodiment, one connecting component (such as a receiving component) may be fixedly mounted on a distal end of a glass barrel. The receiving component may directly receive and engage the barrel tip with the integrated retraction mechanism. Alternatively the barrel adapter may include an additional connecting component (such as a mating component) which is used to engage the receiving component. Other optional components, such as elastomeric seals, which are known to one having ordinary skill in the art, may be necessary and incorporated into the device to facilitate the connection between the barrel adapter and the barrel. The barrel adapters, while including essentially the same components regardless of needle dimensions, may be customized to facilitate the complete refraction of the needle into the barrel. For example, longer biasing members (e.g., longer springs) may necessarily be selected or modified to facilitate refraction of a longer needle, as would be readily appreciated by one ordinarily skilled in the art.

The embodiments of the present invention provide configurations which may also utilize materials and components which are readily employable for pharmaceutical use, many of which are increasingly considered off-the-shelf or standard components. This reduces overall manufacturing costs, streamlines assembly processes, and avoids unnecessary regulatory concerns often associated with the use of non-standard materials and components. Additionally, the present invention provides components and devices which are aesthetically-similar to conventional syringes, which do not have needle retraction mechanisms, are ergonomically attractive to end-users, such as a medical practitioners and self-administering patients, and provide highly desired integrated safety features. These embodiments, accordingly, provide novel and cost-efficient components and devices which are readily integrated into drug filling processes.

Furthermore, the embodiments of the present invention provide efficient delivery of fluid contents, thereby minimizing wastage of pharmaceutical drugs. They similarly provide configurations which minimize dead-space, e.g., interstitial voids within the syringe barrel, which reduces or eliminates the capture of undesirable air bubbles during the assembly or filling process. These aspects of the present invention may provide highly desired functional and aesthetic characteristics, and may be modified to produce a range of different configurations.

For example, the embodiments of the present invention may utilize a flared needle, i.e., a needle that is flared at its proximal end to reduce the dead-space within the drug chamber of the barrel. The flaring of the needle may be configured to be a line-to-line fit with the distal face of the needle seal, or an interference fit with that surface. This could additionally or alternatively be achieved by pre-piercing the needle seal with a solid needle or trocar. Because of this configuration, minimal or no dead-space is created between the needle and the needle seal, which provides improved accuracy of drug filling and dose delivery. This configuration of the present invention also greatly simplifies manufacturing processes. The needle seal may be pre-drilled to accept the needle or may be pierced by the needle at assembly. In either of these configurations, there are no additional components necessary to mate the needle to the needle seal or enable any of the features of the barrel adapter, retraction mechanism, or safety syringe. The needle may also be a standard, non-flared needle, depending on the desired configuration and mating between the needle and the needle seal.

The syringes of the present invention enable drug delivery with integrated safety as they prevent accidental exposure to the needle, as is common with needle stick injuries. As described above and detailed in the figures, a user may utilize the safety syringes of the present invention to perform the stages of drug delivery, including: needle injection, drug dose delivery, retraction activation, and needle retraction. Notably, the components of the barrel adapters of the present invention are held substantially in position through the stages of needle injection and drug dose delivery. This novel feature enables the barrel to be graduated, i.e., marked with volumes, because the reference point for end of dose is constant. The substantially stable and constant position of the needle seal through the stages of needle injection and dose delivery, the stages during which some amount of drug may still reside in the drug chamber of the barrel, enables the identification of "zero volume," i.e., the point where there is no drug left in the chamber. Moving proximally from this point along the axial length of the barrel, drug volumes can be calculated based on the diameter of the barrel and can be marked along the length of the barrel. Several methodologies exist for measuring volumes and marking graduations on cylindrical barrels, which are known to one having ordinary skill in the art. Accordingly, the novel design of the barrel adapters and syringes of the present invention enable the use of graduated syringe barrels. This is a desirable feature for syringe users, including medical professionals and patients.

By integrating one or more locking systems to prevent or at least minimize syringe re-use and/or needle stick injury, the embodiments of the present invention provide highly desirable products which are cost-efficient to manufacture and easy-to-use by medical practitioners and self-administering patients. Such locking systems may include, for example, needle retraction mechanisms and/or arrangements that block a retracted needle from again extending from the end of the syringe. The novel features and functionality of the barrel adapters and syringes of the present invention provide a number of safety advantages to the user. For example, the locking mechanism may be configured to provide visual, audible, and/or tactile feedback to the user that the drug dose has been fully delivered, the retraction mechanism has been activated, the needle has been retracted, and that the syringe is safe for disposal. The components of the present invention are also configured such that there is increased destruction of the components, and the syringe overall, at the end of use. Such integrated safety and destruction prevents the reusability of the syringe and increases the safety profile of the device. For example, an optional needle blocking mechanism may be configured to prevent the needle from translating in the proximal direction out of the barrel tip after needle retraction. Additionally or alternatively, one of the existing components may function as a needle blocking mechanism after retraction of the needle has occurred, as described further herein. Depression of the plunger rod and axial translation of the needle in the distal direction after retraction, in this configuration, will result in the needle becoming bent within the barrel as a force is applied by the user. Another safety feature enabled by the present invention is the ability to control the rate of retraction of the needle. Controlled needle retraction prevents injury to the patient after the drug dose has been delivered. This can be facilitated by active components, such as one or more friction members limiting the rate of expansion of the biasing member upon retraction activation, or by passive components, such as the selection of biasing members which have slower expansion. In the embodiment shown in FIG. 1, the retraction is controlled by plunger rod and plunger seal. At the end of dose, upon activation of needle retraction, the user is still in contact and applying force to the proximal end of the plunger rod. As the biasing member is caused to expand, it imposes an axial force in the proximal direction to retraction the needle and/or needle subassembly. This action conveys the force to the plunger seal, which is in contact with the needle seal at the end of dose, and the plunger rod. The friction caused by the needle seal and the plunger seal against the interior of the barrel limits the rate of retraction of the needle subassembly. As the user reduces the force they apply on the plunger rod, they can also control the rate of needle retraction. This controlled retraction is highly desired by syringe users as it increases the safety and reduces the pain felt to the patient.

The embodiments of the present invention are detailed further herein with respect to the attached figures. It is to be understood that these are merely non-limiting embodiments and that other similar embodiments are within the contemplation of the present invention and within the breadth and scope of the present disclosure.

As used herein to describe the syringe, barrel, barrel adapter, or any of the relative positions of the components of the present invention, the terms "axial" or "axially" refer generally to a longitudinal axis "A" around which syringe or barrel is preferably formed although not necessarily symmetrically there-around. The term "radial" refers generally to a direction normal to the axis "A". The terms "proximal," "rear," "rearward," "back," or "backward" refer generally to an axial direction in the direction of P shown in FIG. 1. The terms "distal," "front," "frontward," "depressed," or "forward" refer generally to an axial direction in the direction of D shown in FIG. 1. It is to be understood that the term "spring" is used herein to suggest a biasing member, such as a substantially spiral-wound coil, that may be compressed and allowed to expand in a given direction. While the spring element such as the arrangement discussed and utilized in the embodiments detailed herein may be utilized, it is within the contemplation of the present invention that other types of biasing members may be readily employed for the same purpose while remaining within the breadth and scope of the present invention. For example, springs such as compression springs, torsion springs, constant force springs, extension springs, and leaf springs, or combinations of different types of springs may be utilized within the scope of the present invention, as would be understood by an ordinarily skilled artisan. Additionally or alternatively, biasing members other than springs may also be employed for similar purposes. Non-limiting examples of biasing members include a spring, elastic or other device for storing releasable energy. In at least one embodiment, however, the biasing member is preferably a spring, such as a compression spring.

As used herein, the term "glass" should be understood to include other similarly non-reactive materials suitable for use in a pharmaceutical grade application that would normally require glass. The term "plastic" may include both thermoplastic and thermosetting polymers. Thermoplastic polymers can be resoftened to their original condition by heat; thermosetting polymers cannot. As used herein, the term "plastic" refers primarily to moldable thermoplastic high polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" does not include either glass or rubbery elastomers that are approved for use in applications where they are in direct contact with therapeutic liquids that can interact with plastic or that can be degraded by substituents that could otherwise enter the liquid from plastic. As used herein, the term "elastomer," "elastomeric" or "elastomeric material" refers primarily to crosslinked thermosetting rubbery polymers that are more easily deformable than plastics but that are approved for use with pharmaceutical grade fluids and are not readily susceptible to leaching or gas migration. As used herein, the term "fluid" refers primarily to liquids, but can also include suspensions of solids dispersed in liquids, and gasses dissolved in or otherwise present together within liquids inside the fluid-containing portions of syringes.

Additionally, the barrel adapters of the present invention utilize materials that are substantially non-reactive with therapeutic fluids or drugs, and are suitable for use in pharmaceutical grade applications. The novel barrel adapters are configured to minimize or eliminate the possibility of contact or interaction between degradable materials, such as certain plastics, with the therapeutic fluids or drugs. The barrel adapters, with adaptable needle retention and retraction mechanisms, also provide fluid pathways from the primary drug chamber to the patient, through the needle, which are substantially absent of degradable materials. Such novel adapter configurations, when integrated into barrels to provide the novel safety syringes of the present invention, provide increased stability and shelf-life parameters to the drug and drug delivery devices. These characteristics are thought to be highly desirable for generally all pharmaceutical treatments, but perhaps especially of value in syringes for use with biologics and other complex therapies. In one embodiment, for example, a metal needle is retained within a glass barrel by an elastomeric needle seal at a proximal end of the needle and by an aperture of a plastic barrel tip at a portion of the needle that is distal to the needle seal, such that the drug fluid pathway contains (and the drug contacts) only glass, elastomer, and metal, without contacting any plastic, as the drug travels from drug chamber to patient. In other embodiments, other material combinations or fewer materials may be utilized for the drug fluid pathway.

One or more embodiments of the present invention may further include certain standard components. For example, the barrel adapter configurations and syringe devices of the present invention may include one or more O-rings. In at least one embodiment, one or more O-rings are employed to seal the barrel tip within the barrel and/or to ensure a sterile environment and container integrity within the drug chamber of the barrel.

Additionally or alternatively, the barrel adapter may include one or more controlling members to facilitate the control of the rate of retraction. Similarly, the barrel adapter may include one or more needle blocking mechanisms, such as clips, flaps, flanges, or the like, which function to prevent the needle from being translated or protruding out of the barrel through the aperture of the barrel tip after the retraction mechanism has been initiated or completed.

Furthermore, the safety syringe may include one or more components for aesthetics, ease-of-use, or other purposes. For example, one or more embodiments of the present invention may include a finger flange. The finger flange may be pre-formed along any portion of the barrel or safety syringe, or may be a separate component that is connected to or affixed to the barrel or safety syringe. In at least one embodiment, the finger flange is a preformed component at the distal end of the barrel. The finger flange may be configured to allow a user to rest their pointer and middle fingers on the flange, and may provide a leverage interface when the user is depressing the plunger with their thumb for injection of the drug. The position, shape, number, and materials for such components may vary, as would be readily appreciated by a skilled artisan, to meet any number of desired characteristics.

Similarly, while the components of the barrel adapter and the safety syringe are described herein as separate components, it is within the contemplation of the present invention that certain groups of these components may be combined to form a single component capable of performing the functions of the individual components. Additionally, as would be appreciated by one having ordinary skill in the art, the components of the safety syringes may be manufactured as individual components or as single components. As described above, the finger flange may be a component that is pre-formed, during the manufacturing process, as a part of the barrel itself. Accordingly, in at least one embodiment, the finger flange may be a glass finger flange extension of the barrel.

Furthermore, while the components of the barrel adapter are described herein as separate components, they may be unified components having multiple functions. As discussed above, the biasing member (e.g., spring) may be compressed in its energized state and the locking mechanism engaged either prior to installation in the barrel tip or after the components have been mounted in the barrel. The configuration of the components and their assembly may vary based on the assembly process, the device parameters, and other desired characteristics.

FIG. 1 shows an isometric view of one embodiment of a safety syringe 10, according to the present invention. In accordance with the invention, a barrel adapter 100 is provided for attachment to a syringe barrel 20 having a plunger assembly 8. The plunger assembly 8 includes a plunger rod 12 and a plunger seal 14. The barrel 20 may be a plastic barrel, a glass barrel, or made of any other known material for use in medical devices. The barrel 20 may be tapered, non-cylindrical, or substantially straight. In an embodiment preferred for manufacturing purposes, the barrel 20 is a straight barrel glass cylinder. The embodiments of the present invention also enable significant other advantages in the marketplace for safety syringes.

For example, one or more embodiments can utilize standard components, such as standard plunger rods, plunger seals, and rigid needle shields, thereby greatly reducing the need for specially-tailored or injection molded components. For example, FIG. 1 shows an embodiment which utilizes a standard plunger rod 12, plunger seal 14, and a rigid needle shield 18, as explained in more detail below, among other possible standard components. The plunger seal 14 may be, for example, an ethylene tetrafluoroethylene (ETFE) coated rubber stopper/seal, such as that which is readily-available under the trade name "FluroTec" from West Pharmaceutical Services, Inc., of Lionville, Pa. Other components may similarly be standard, off-the-shelf components, providing a great advantage of the embodiments of the present invention. This advantage of the embodiments of the present invention provides valuable manufacturing efficiencies and operational cost-savings.

Figure 2A:
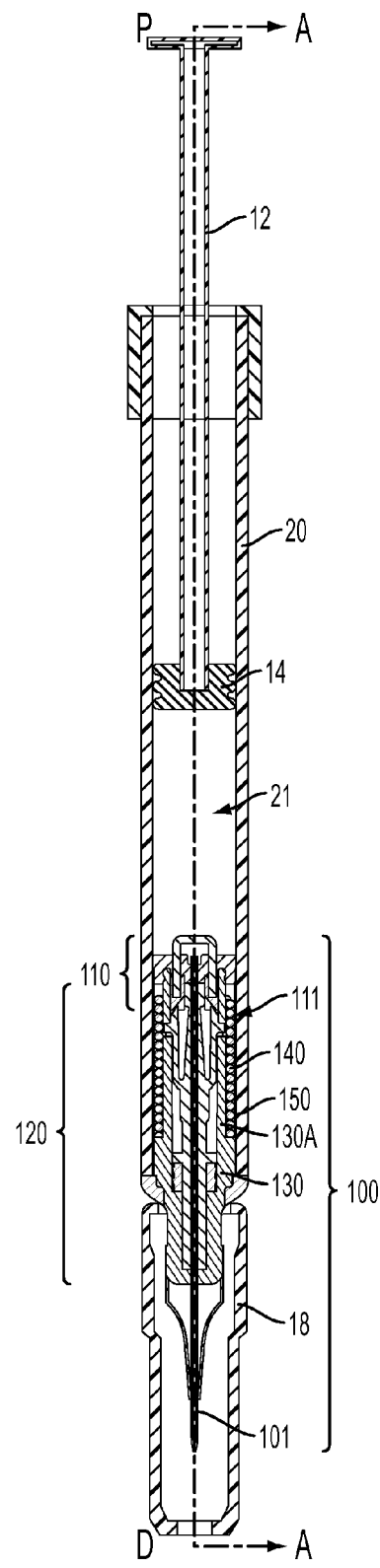
FIG. 2A is a cross-sectional view taken along line A-A of the embodiment shown in FIG. 1.
Figure 2B:
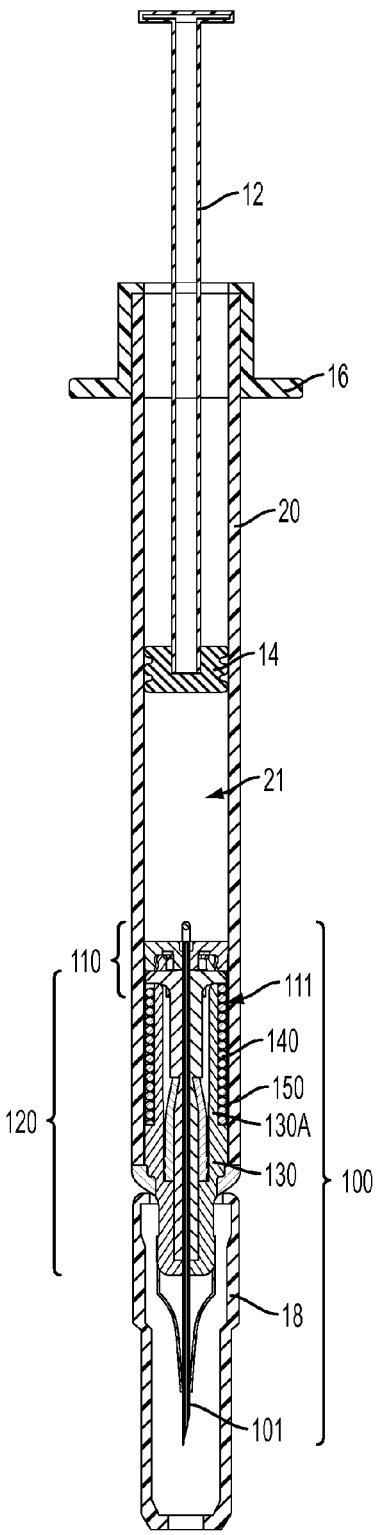
FIG. 2B is a 90 degree rotated cross-sectional view taken along line A-A in FIG. 2A.
Figure 3:
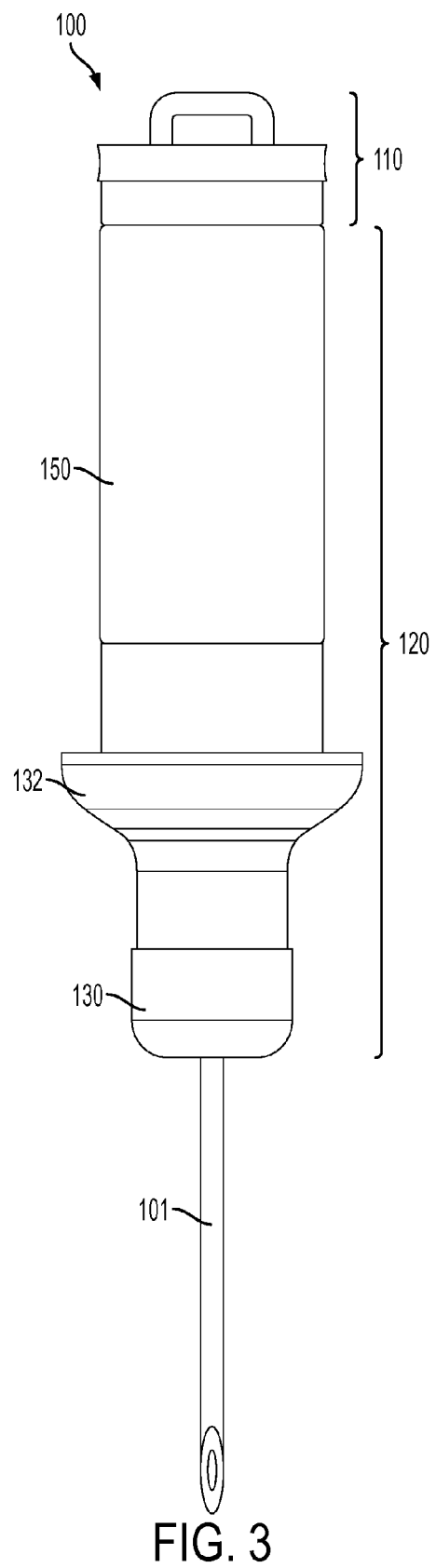
FIG. 3 is an enlarged side view of a barrel adapter according to the embodiment of FIG. 1.
Figure 5A:
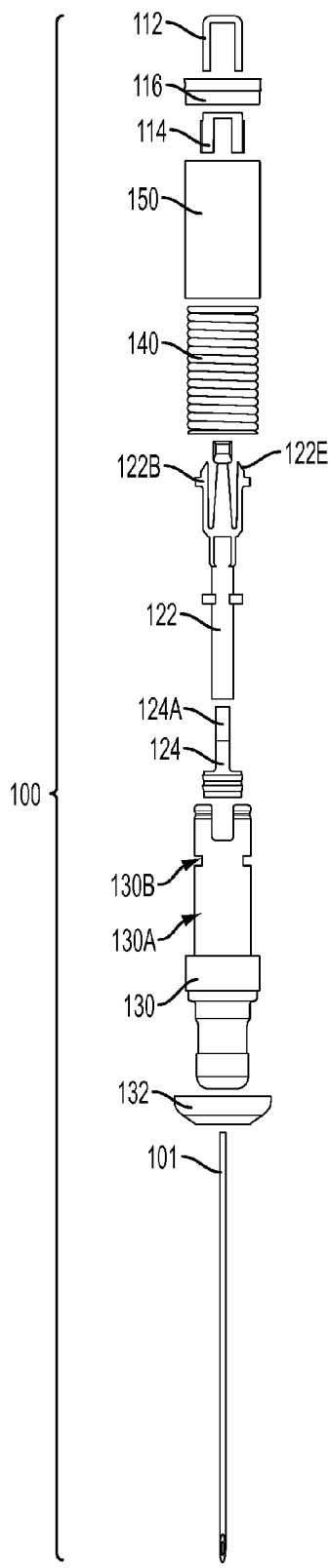
FIG. 5A is an exploded side view of the barrel adapter of FIG. 3.
Figure 5B:
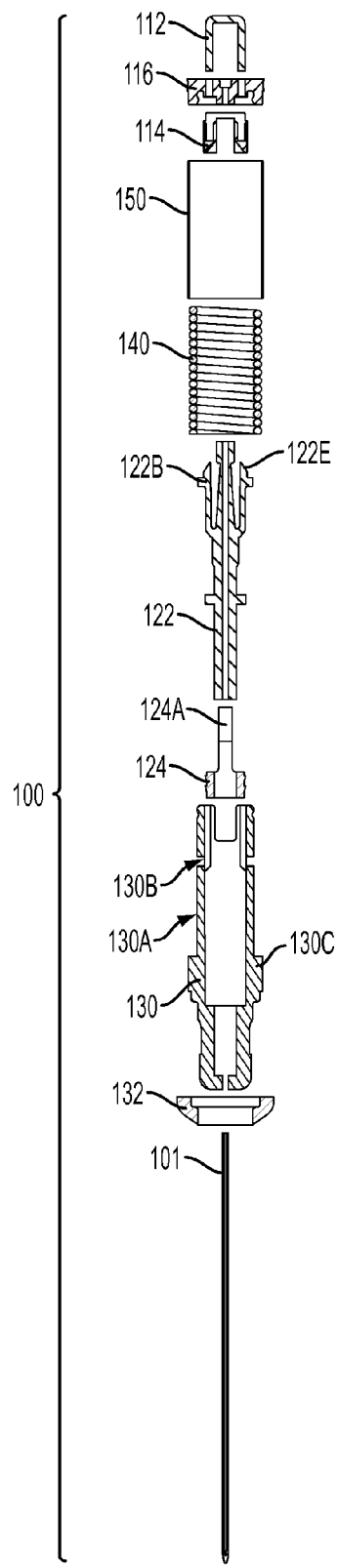
FIG. 5B is a cross-sectional view of the exploded barrel adapter of FIG. 5A.

The barrel adapter 100 is shown in cross-section and assembled with a safety syringe 10 in FIGS. 2A and 2B, in assembled form in FIG. 3, and in exploded form in FIGS. 5A and 5B. The barrel adapter 100 facilitates mounting of a needle 101 (visible in FIGS. 2A and 2B) to the syringe barrel 20. The barrel adapter 100 includes a barrel tip 130 and a needle retraction mechanism 111, which includes a needle subassembly 120, an actuator subassembly 110, a biasing member 140, and an actuable locking arrangement disposed to maintain the biasing member 140 in an energized position. The barrel tip 130 typically presents a distal end to the safety syringe 10 when coupled to the syringe barrel 20, the needle 101 extending through the distal end of the barrel tip 130 during injection of a medicament. The barrel tip 130 may further include a structure that forms a part of the needle retraction mechanism 111, such as a sleeve 150 and/or a spring guide 130A, as will be explained below.

The barrel adapter 100 may be mounted to the syringe barrel 20 by any appropriate coupling arrangement, as will be understood by those of skill in the art. More specifically, as an advantage of the embodiments of the present invention, the barrel tip 130 of the barrel adapter 100 may be configured to mate with any standard barrel 20 by any appropriate method. For example, the barrel adapter 100 may be coupled to the syringe barrel 20 by a coupling structure that may be separate from components of the barrel adapter 100 and syringe barrel 20, or integral with the barrel adapter 100 and the syringe barrel 20. Moreover, the barrel adapter 100 may be coupled to the syringe barrel 20 during the syringe manufacturing process or just prior to use. By way of example only, the barrel adapter 100 may be coupled to the syringe barrel 20 by an interference fit, spin welding, adhesive or glue, or like mechanism during the syringe manufacturing process. Alternately, for example, the syringe barrel 20 and barrel adapter 100 may include mating threads or a Luer locking arrangement, such that the barrel adapter 100 may be coupled to the syringe barrel 20 just prior to use.

FIG. 3 shows an enlarged view of a barrel adapter, according to at least one embodiment of the present invention. The barrel adapter 100 includes a needle retraction mechanism 111 having a needle subassembly 120 and an actuator subassembly 110. The needle 101 passes through the barrel adapter 100 such that a distal end of the needle 101 extends distally from a barrel tip 130 of the barrel adapter 100 and a proximal end of the needle 101 extends proximally from a needle subassembly 120 of the barrel adapter 100. The needle 101 thus creates a fluid path 101A for drug delivery from a drug chamber 21 (shown in FIG. 1) to the body of the user.

Figure 4A:
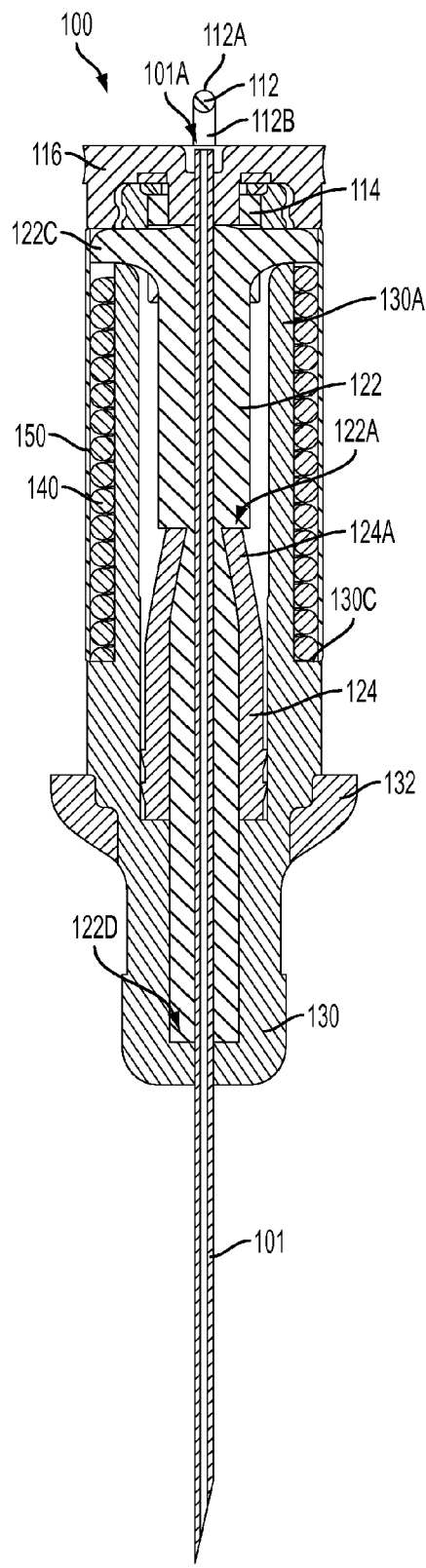
FIG. 4A is a cross-sectional view of the barrel adapter of FIG. 3.
Figure 4B:
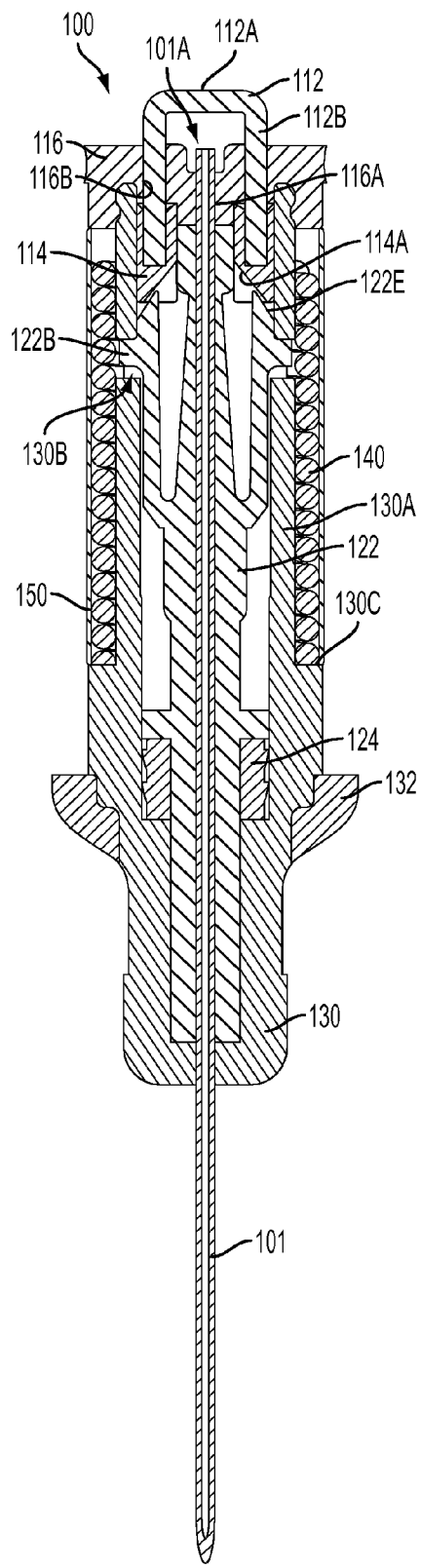
FIG. 4B is a 90 degree rotated cross-sectional view of the barrel adapter of FIGS. 3 and 4A.

FIGS. 4A and 4B show cross-sectional views of the barrel adapter 100, according to one embodiment of the present invention. The needle subassembly includes needle-overmold ("NOM") 122, needle 101, and, optionally, a needle blocking mechanism adapted to block the needle 101 within the barrel adapter 100 following retraction. In the illustrated embodiment, the needle blocking mechanism includes a clip 124. Clip 124 may initially slidably or removably engage NOM 122 such as, for example, at an engagement between clip arms 124A and NOM engagement surface 122A (visible in FIG. 4A). Upon retraction of the needle 101 and axial translation in the proximal direction of NOM 122, the clip arms 124A may flex inwards (i.e., towards the axis A) to contact NOM tip 122D in a needle blocking configuration. Such a needle blocking configuration prevents axial travel in the distal direction after retraction and retains the needle 101 substantially within the barrel tip 130 and/or the barrel 20 of the syringe 10.

Turning to FIG. 4B, the barrel adapter 100 further includes an actuable locking arrangement disposed to maintain a biasing member 140 in an energized position until actuated by the actuator subassembly to retract the needle 101. In the illustrated embodiment, the barrel tip 130 includes a spring guide 130A. In order to maintain the biasing member 140 in its initial energized position, the NOM 122 may initially be disposed in engagement with the barrel tip 130, sandwiching the energized biasing member 140 between one or more ledges 122C of the NOM 122 and an engagement surface 130C of the barrel tip 130. In one such embodiment of the actuable locking arrangement, the spring guide 130A of the barrel tip 130 may include one or more locking recesses or locking ledges 130B adapted to receive, for example, locking prongs 122B of NOM 122. As will be described further below, upon substantial completion of drug delivery through the fluid path, i.e., needle 101, the actuable locking arrangement may be actuated by the actuator subassembly to cause the locking prongs 122B to move inward and release from the locking recesses 130B of the barrel tip 130 to then permit the biasing member 140 to deenergize, exerting a force on the ledge(s) 122C of the NOM 122 to retract the needle 101.

The actuator subassembly 110 is disposed to actuate the actuable locking arrangement to permit the biasing member 140 to deenergize, retracting the needle 101. In the illustrated embodiment, the actuator subassembly 110 includes a needle seal 116, a push bar 112, and an actuator 114. In some embodiments, the push bar 112 is slidably disposed relative to the needle seal 116. In at least one embodiment, push bar 112 resides at least partially within a proximal end of the needle seal 116 and in contact with actuator 114 which resides distal to needle seal 116. Depression of the push bar in such a configuration is capable of contacting and depressing (or axially translating in the distal direction) the actuator 114. In at least an initial configuration, such as for needle insertion into the body of a user, the actuator subassembly 110 may reside proximal to and either in contact with or adjacent to the needle subassembly 120.

An embodiment of the actuator subassembly 110 is shown in greater detail in FIGS. 7A and 7B. In at least one embodiment, push bar 112 includes a proximal contact surface 112A and one or more force transfer elements 112B that extend through corresponding throughways 116B in the needle seal 116. In assembly, the force transfer element 112B extending through the needle seal 116 engage the actuator 114 such that axial movement of the push bar 112 causes axial movement of the actuator 114. In this regard, the push bar 112 and the actuator 114 may be engaged and coupled together during the assembly process or the components may be disposed such assembly such that some axial movement of the push bar 112 is permitted before it engages and causes axial movement of the actuator 114. It is noted that the needle seal 116 may additionally include an opening 116A through which the proximal end of the needle 101 extends to establish a path for drug delivery.

Figure 10A:
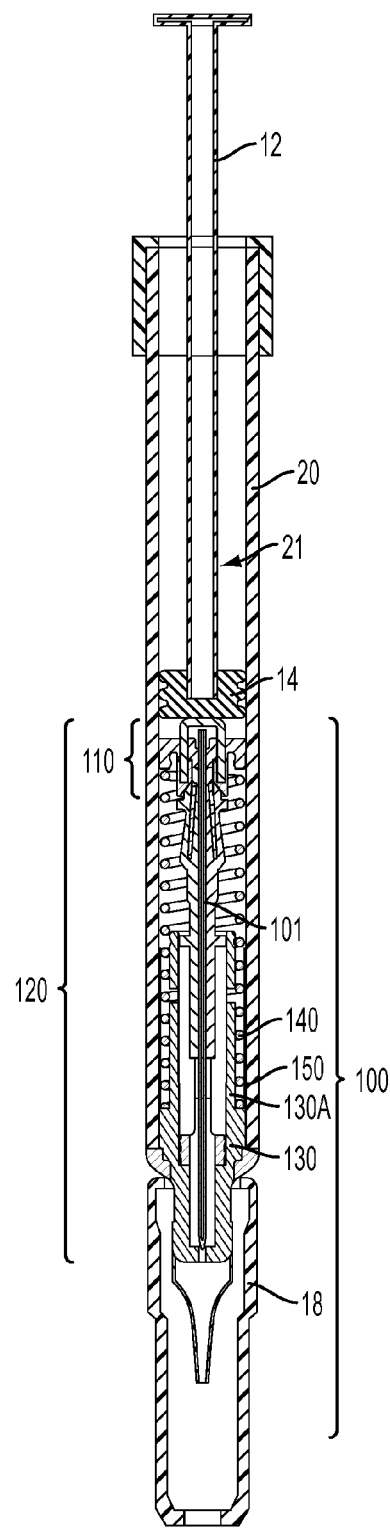
FIG. 10A is a cross-sectional view of a syringe similar to FIG. 2A, during the retraction process.
Figure 10B:
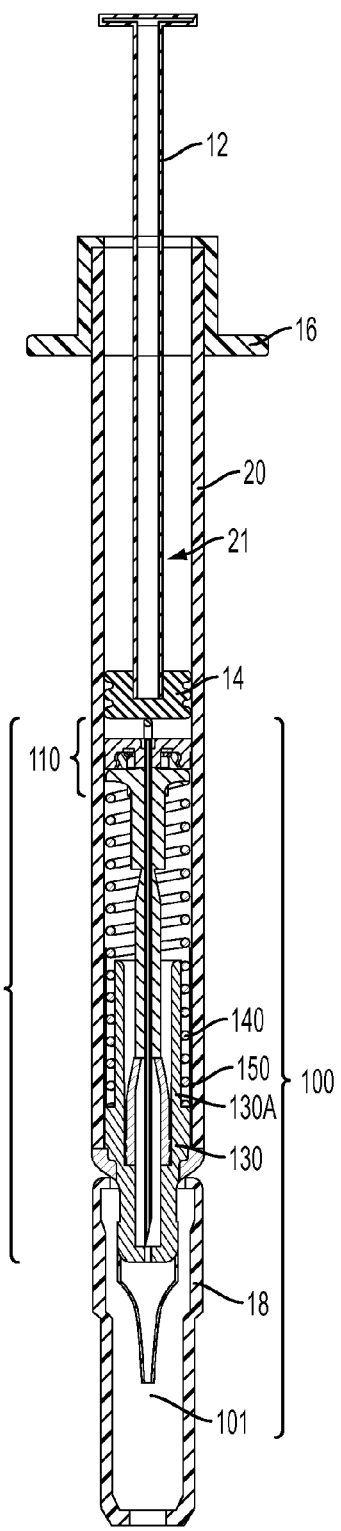
FIG. 10B is a cross-sectional view of the syringe of FIG. 10A taken at 90 degrees to the view of FIG. 10A.

The actuator 114 includes one or more actuating surfaces 114A disposed to engage and actuate the actuable locking arrangement to actuate the needle retraction mechanism 111. To facilitate operation, in the illustrated embodiment, the actuating surfaces 114A are sloped and disposed to engage corresponding sloped surfaces 122E of the locking prongs 122B of the NOM 122. In this way the axial movement of the actuator 114 causes the actuating surfaces 114A to slide along the sloped surfaces 122E of the locking prongs 122B to urge the locking prongs 122B radially inward, causing disengagement of the locking prongs 122B from the locking recesses 130B of the barrel tip 130. As a result, the biasing member 140 is permitted to at least partially deenergize, retracting the needle 101 (see FIGS. 10A and 10B).

In other words, in operation, when the plunger seal 14 is caused to contact push bar 112. As a result, further depression of the plunger seal 14 during drug delivery causes axial translation of the push bar 112 in the distal direction at least partially through, or further through, needle seal 116. With the push bar 112 in contact with the actuator 114, axial translation of the push bar 112 results in axial translation of the actuator 114. Axial translation of the actuator 114 causes contact with, and flexion of, locking prongs 122B of NOM 122 to disengage the locking prongs 122B from the corresponding locking recesses 130B of the spring guide 130A.

Upon disengagement of the locking arrangement between the locking prongs 122B from the corresponding locking recesses 130B, biasing member 140 is permitted to expand in the proximal direction from its initial energized state to a reduced or de-energized state. This expansion in the proximal direction of the biasing member 140 pushes upon a ledge 122C of NOM 122 causing NOM 122 and needle 101 to translate in the proximal direction to a retracted state. As described above, upon retraction of the needle 101 and axial translation in the proximal direction of NOM 122, the clip arms 124A may flex inwards (i.e., towards the axis A) to contact NOM tip 122D in a needle blocking configuration. Such a needle blocking configuration prevents axial travel in the distal direction after retraction and retains the needle 101 substantially within the barrel tip 130 and/or the barrel of the syringe. In at least one embodiment of the present invention, push bar 112 and actuator 114 are a unified or single component.

FIGS. 6A and 6B show a partial assembly of the needle subassembly, according to one embodiment, in which the needle 101 passes through and at least partially resides within NOM 122. Clip 124 engages NOM 122, for example, at an outer surface of NOM 122. Clip 124 may initially slidably or removably engage NOM 122 such as, for example, at an engagement between clip arms 124A and NOM engagement surface 122A.

Returning to FIGS. 5A and 5B, additional features of the arrangement are apparent. For example, an optional sleeve 150 may be utilized within the barrel adapter to hide the functional retraction components of the barrel adapter from view at least at an initial non-refracted stage. In at least one embodiment, the biasing member 140 may reside between the spring guide 130A and sleeve 150, while the NOM 122, clip 124, and needle 101 reside at least partially within spring guide 130A. FIGS. 5A and 5B also show a separate barrel tip cap 132 which may be utilized, for example, to facilitate assembly and manufacturing of the barrel adapters and syringes of the present invention. It will readily be understood that such components may be incorporated or be an aspect of other components. For example, barrel tip cap 132 may be a pre-formed aspect of barrel tip 130.

Figure 8C:
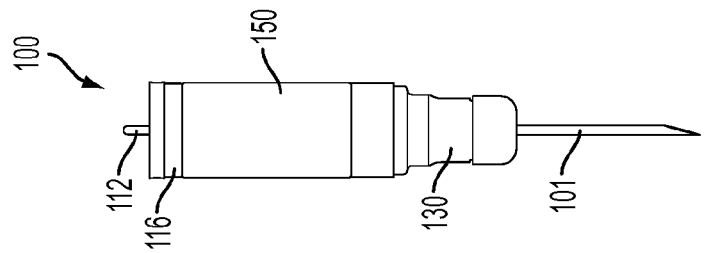
FIGS. 8A-8C show a partial assembly process of a barrel adapter having a needle subassembly and an actuator subassembly, according to at least one embodiment of the present invention.
Figure 8B:
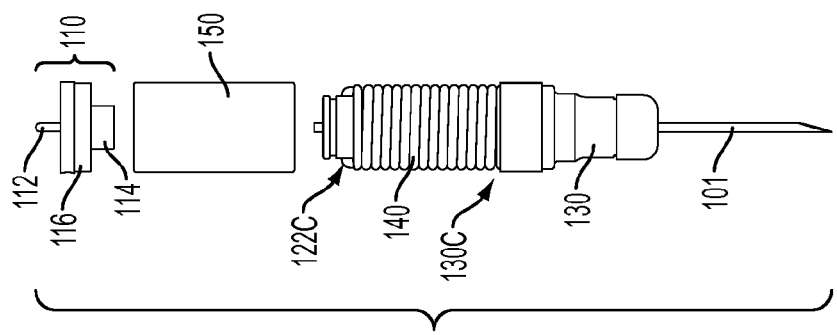
Figure 8A:
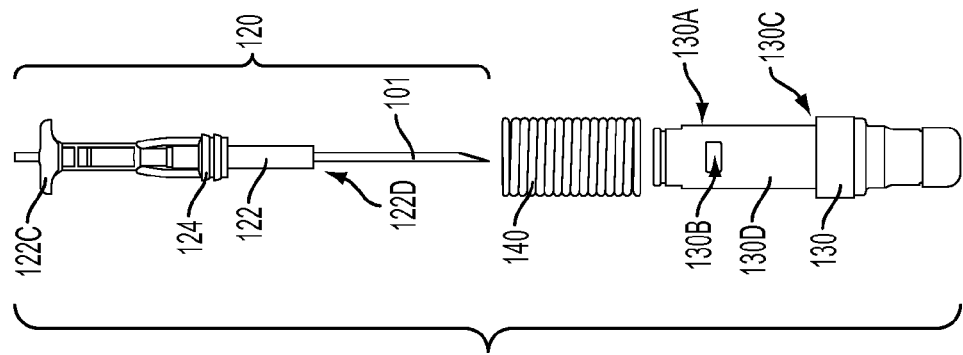

FIGS. 8A-8C show a further partial assembly of a barrel adapter 100 according to at least one embodiment of the present invention. The needle subassembly 120 having NOM 122, needle 101, and clip 124 may be inserted within a spring guide 130A of barrel tip 130. A biasing member 140 may reside, for example, around the exterior surface of the spring guide 130A and held in an initially energized state between engagement surface 130C of barrel tip 130 and ledge 122C of NOM 122. Such components are held in the initial locking arrangement and energized state by detachable locking engagement between NOM 122 and spring guide 130A. Such locking engagement may be between, for example, locking prongs 122B of NOM 122 and corresponding locking recesses 130B of the spring guide 130A. This is more evident by the arrangement shown in FIG. 8A. FIG. 8B shows such components assembled and ready for the next stage of assembly. An optional sleeve 150 may be placed around biasing member 140 to at least initially hide the functional components of the retraction mechanism. A needle subassembly 110 having a needle seal 116, a push bar 112, and an actuator 114 may be attached such that the needle 101 extends at least partially proximally through needle seal 116. The full assembly of the barrel adapter 100, according to one embodiment, is shown in FIG. 8C.

Figure 9D:
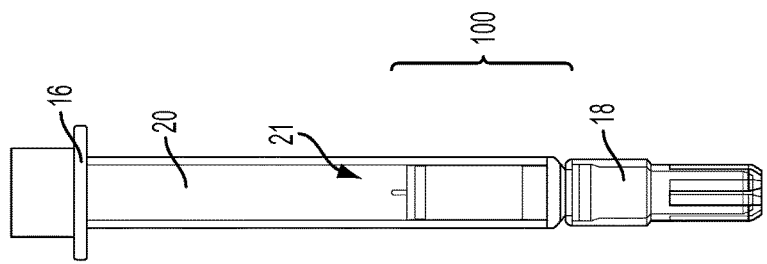
FIGS. 9A-9D show a partial assembly process of a safety syringe including a barrel adapter having a needle subassembly and an actuator subassembly, according to at least one embodiment of the present invention.
Figure 9C:
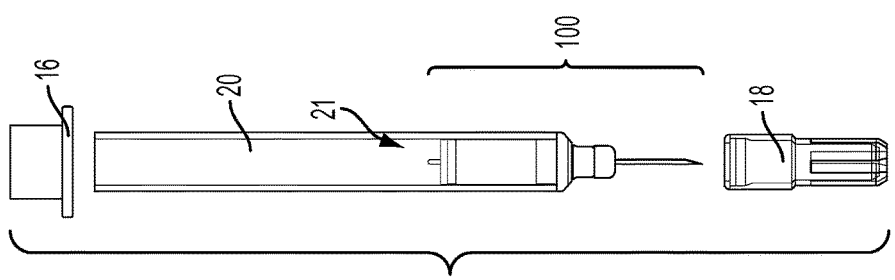
Figure 9B:
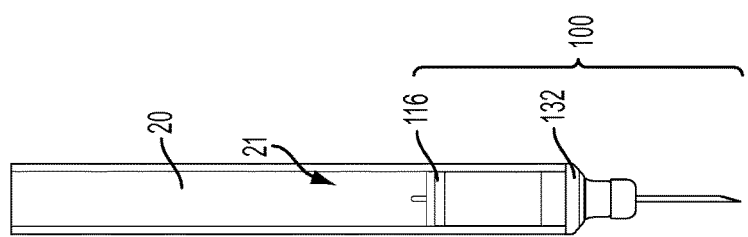
Figure 9A:
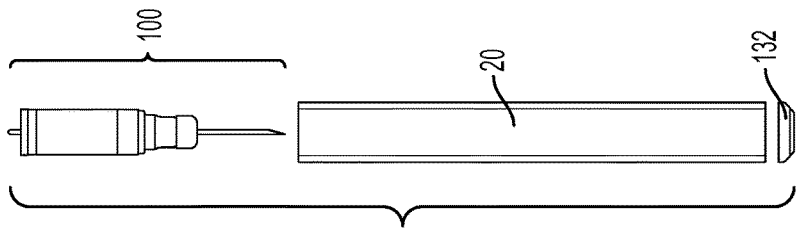

The barrel adapter 100 may then be integrated into a barrel 20 to produce a safety syringe 10. As shown in FIG. 9A, the barrel adapter 100 may be inserted through the proximal end of the barrel 20 and then attached at the distal end of the barrel 20 by a barrel tip cap 132. Alternatively, the barrel adapter 100 may be attached directly to the barrel 20 at least partially through or at the distal end of the barrel 20. As described above, the barrel tip cap 132 may be a unified aspect of barrel tip 130. FIG. 9B shows the barrel adapter 100 assembled to a barrel 20. The interior portion of the barrel 20 just proximal to needle seal 116 is generally defined as a drug chamber 21 within which a drug fluid may be filled for drug delivery. FIGS. 9C and 9D show the assembly or attachment of certain standard optional components including flange 16 and rigid needle shield ("RNS") 18. A plunger assembly having a plunger seal and plunger rod (shown in FIGS. 1, 2A and 2B) may be inserted into the proximal end of the barrel 20 to complete the assembly of the drug syringe 10.

The needle retraction mechanism 111 may be actuated by any appropriate trigger. For example, in the illustrated embodiment, the needle retraction mechanism 111 is actuated by movement of the plunger seal 14 into contact with the needle subassembly 110. Upon disengagement of the locking arrangement and activation of the retraction mechanism, the biasing member 140 is allowed to expand causing the needle subassembly 110 to retract in the proximal direction substantially along a longitudinal axis of the barrel 20. In some embodiments of the present invention, the entire needle subassembly 110 is caused to retract, while in other embodiments only certain components thereof, including the needle 101, are caused to retract upon release of the locking arrangement and expansion of the proximally-biased biasing member (e.g., spring or springs) 140. After retraction of the needle 101 has been initiated or completed, clip 124 may function as a needle blocking mechanism to prevent the needle 101 from translating in the distal direction and out of the barrel tip 130. As stated above, other standard components may be utilized in the assembly of the safety syringes, such as O-ring 36.

A drug or pharmaceutical compound may be contained in the barrel 20 proximally of the needle seal 116. As would be appreciated by an ordinarily skilled artisan, the drug may be a solution, a powder, a suspension, or the like, or any combination thereof. The needle seal 116 has an aperture pass-through at its center (e.g., at substantially the longitudinal axis of these components and the barrel 20). This aperture may have a diameter equal to the diameter of the needle 101, such that the needle 101 is retained in position within the needle seal 116 during an initial injection stage and allowed to axially translate in the proximal direction upon activation of the retraction mechanism. Alternatively, the needle seal 116 may not initially have an aperture prior to positioning of the needle 101 within the needle seal 116 at assembly. In this configuration, the needle 101 may be pushed through the needle seal 116 at assembly and create a line-to-line or interference fit, thereby ensuring a tight seal between the components and minimal or no dead-space.

At the end of drug delivery, the force applied by the user to axially translate the plunger seal 14 and plunger rod 12 may be used to disengage the locking arrangement and activate the retraction mechanism. For example, the plunger seal 14 may be made to contact the needle seal 116 and/or push bar 112 such that force applied to the plunger rod 12 by a user is applied to the plunger seal 14 and transferred, at least in part, to the needle seal 116 and/or push bar 112. The force imparted to the needle seal 116 and/or push bar 112 may similarly be transferred, at least in part, to initiate the release of the locking arrangement as described above. By releasing the locking arrangement, the biasing member (e.g., spring or springs) 140 is allowed to expand and retract the needle subassembly 110 and/or needle 101 in the proximal direction substantially along a longitudinal axis of the barrel 20.

Turning now to FIGS. 11-19B, there is illustrated an alternate embodiment of a barrel adapter 200 according to aspects of the invention and a safety syringe 10 incorporating the barrel adapter 200. For ease of explanation, those components of the safety syringe 10 that are similar to those of the embodiment of FIGS. 1-10B are identified with the same reference numerals. More specifically, the syringe 10 includes a syringe barrel 20 and plunger assembly 8. The plunger assembly 8 includes a plunger rod 12 in conjunction with a plunger seal 14 disposed within the syringe barrel 20.

In as much as many of the aspects of the barrel adapter 200 are similar to those of the embodiment of FIGS. 1-10B, the following discussion will concentrate on those aspects of the barrel adapter 200 insofar as they differ from the barrel adapter 100. As a result, those of skill in the art will appreciate that similar materials and assembly processes may be utilized in the fabrication of the barrel adapter 200, and that the barrel adapter 200 provides similar advantages and features to those of the barrel adapter 100. The embodiment of FIGS. 11-19B, however may provide addition advantages in the fabrication and assembly of the barrel adapter 200 and a safety syringe 10 incorporating the same.

Figure 13:
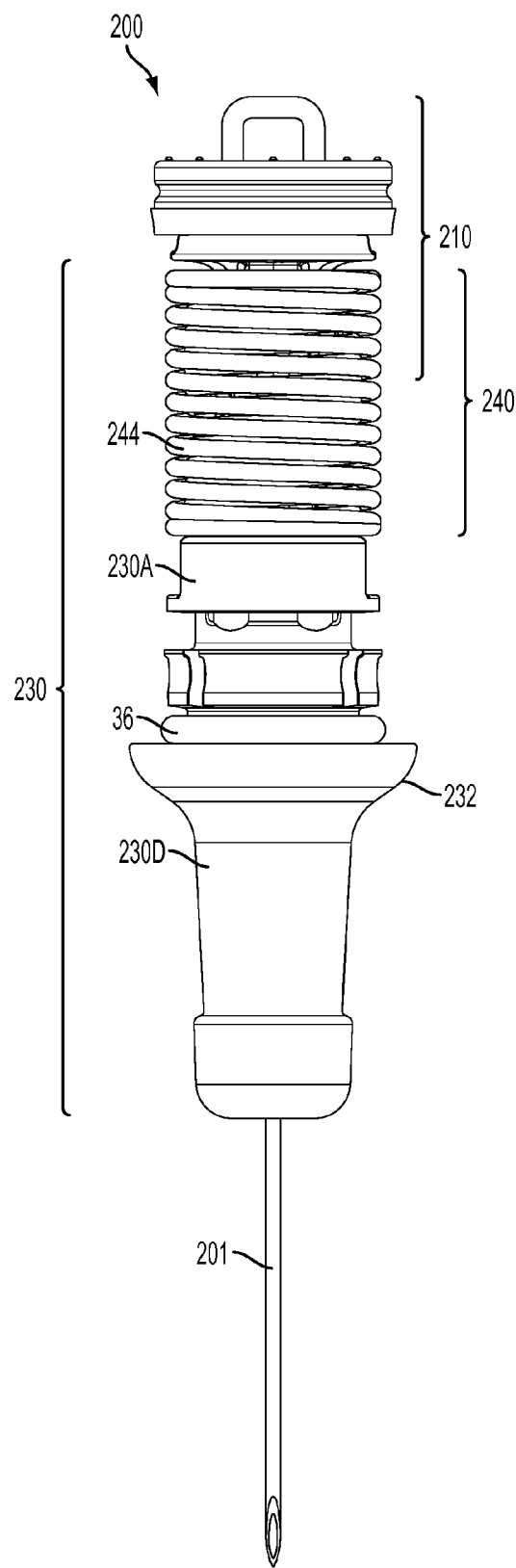
FIG. 13 is an enlarged side view of a barrel adapter according to the embodiment of FIG. 11.
Figure 14A:
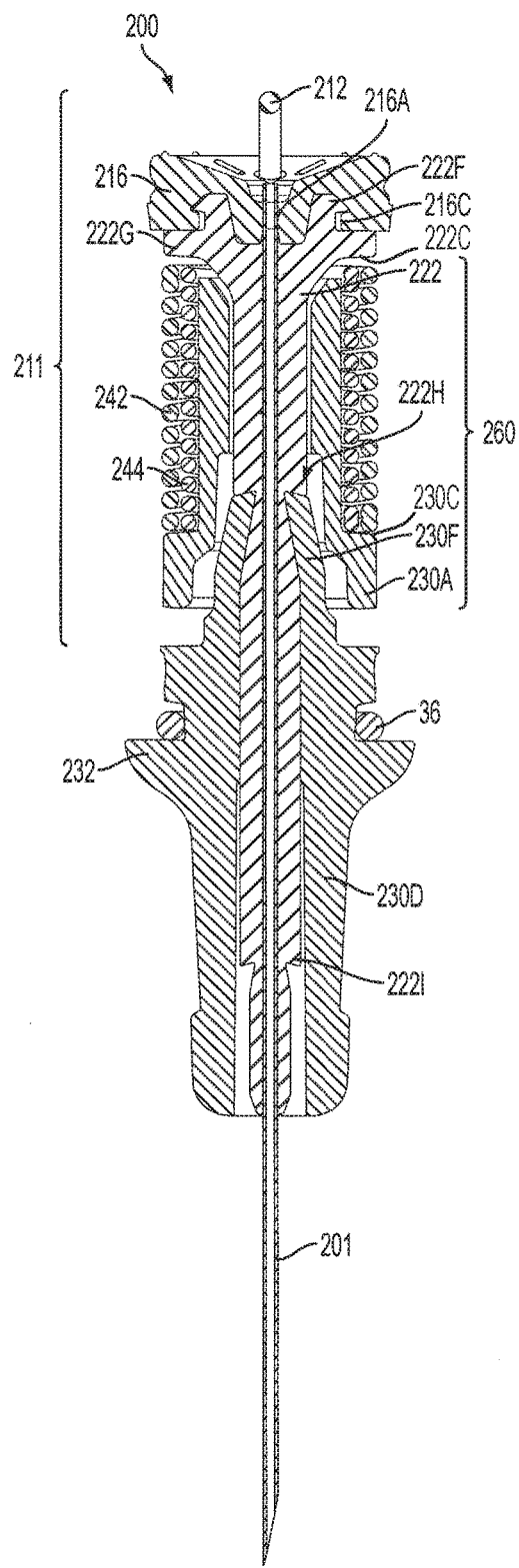
FIG. 14A is a cross-sectional view of the barrel adapter of FIG. 13.
Figure 14B:
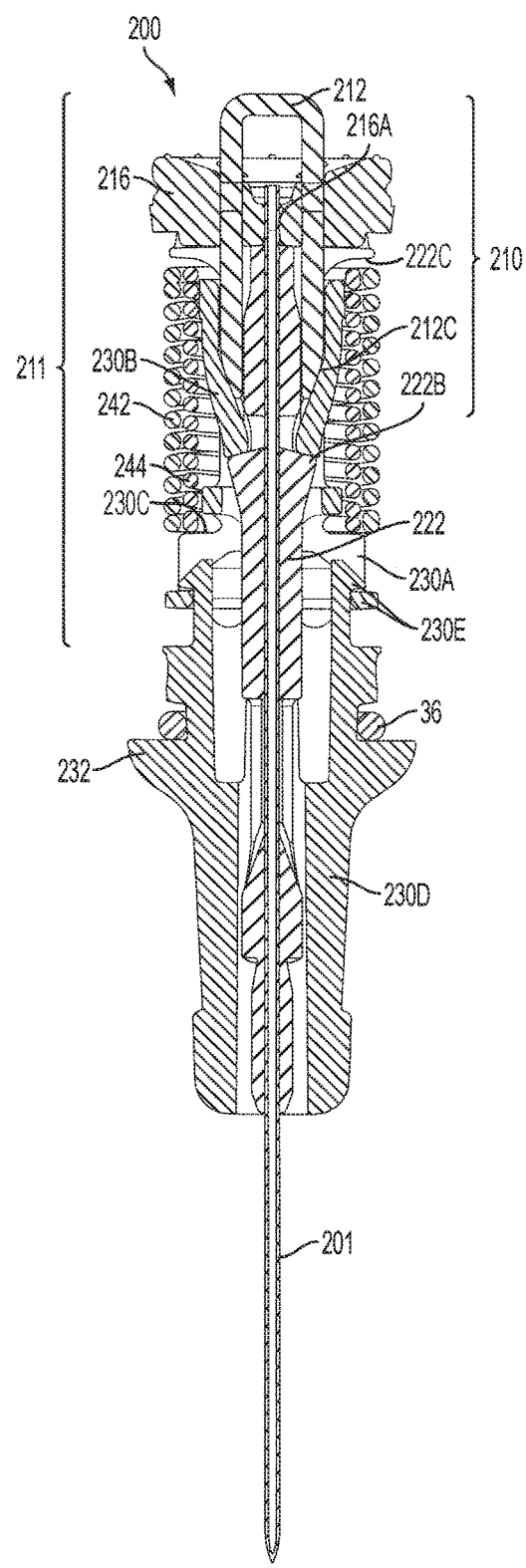
FIG. 14B is a 90 degree rotated cross-sectional view of the barrel adapter of FIGS. 13 and 14A.
Figure 15A:
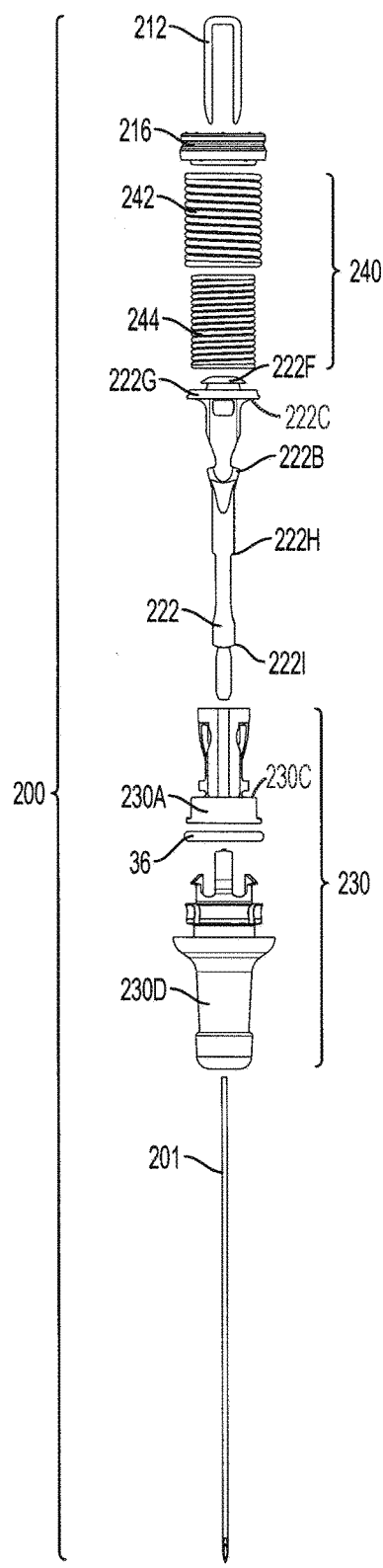
FIG. 15A is an exploded side view of the barrel adapter of FIG. 13.
Figure 15B:
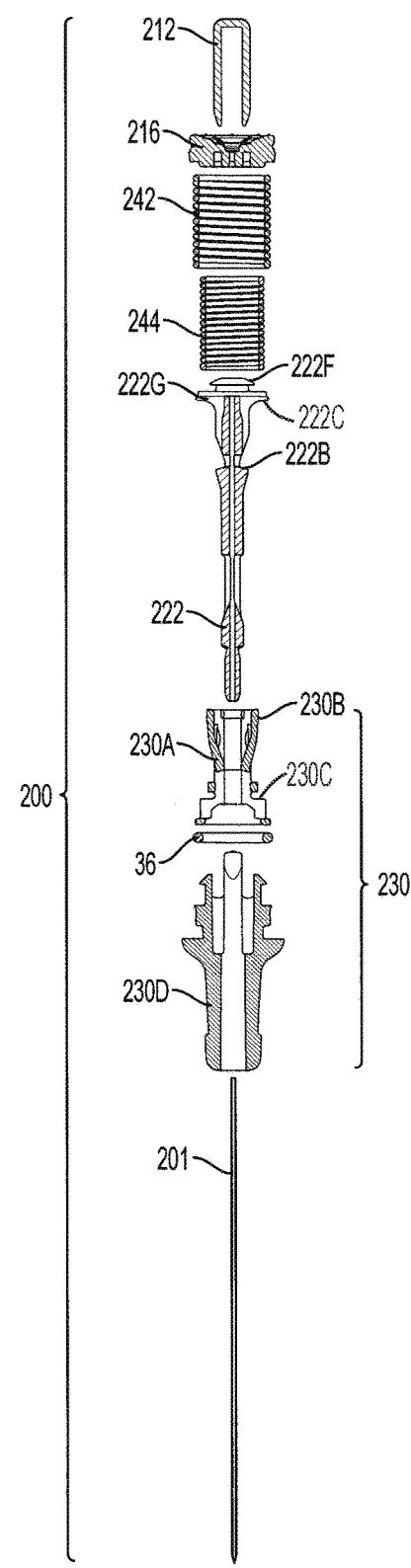
FIG. 15B is a cross-sectional view of the exploded barrel adapter of FIG. 15A.

Turning to FIGS. 13 and 14A-14B, there is shown a barrel adapter 200 according to aspects of the invention. The barrel adapter 200 includes a barrel tip 230, and a needle retraction mechanism 211. The needle retraction mechanism 211 includes a needle subassembly 220, a needle refraction subassembly 260, and an actuator subassembly 210.

Figure 16C:
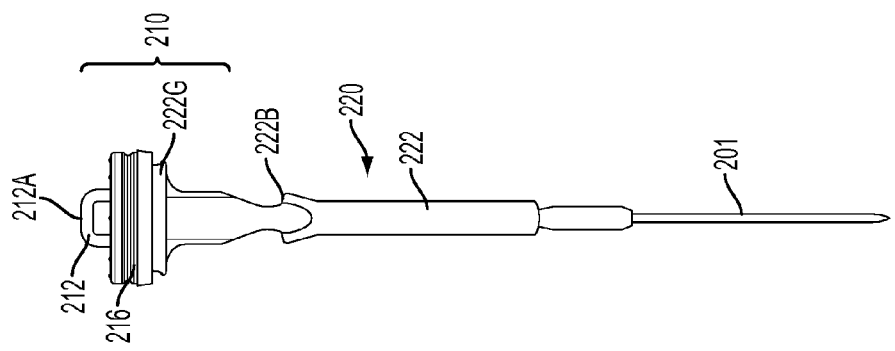
FIG. 16C is an enlarged assembled view of the needle subassembly and actuator subassembly component of the barrel adapter according to the embodiment of FIGS. 16A and 16B.
Figure 16B:
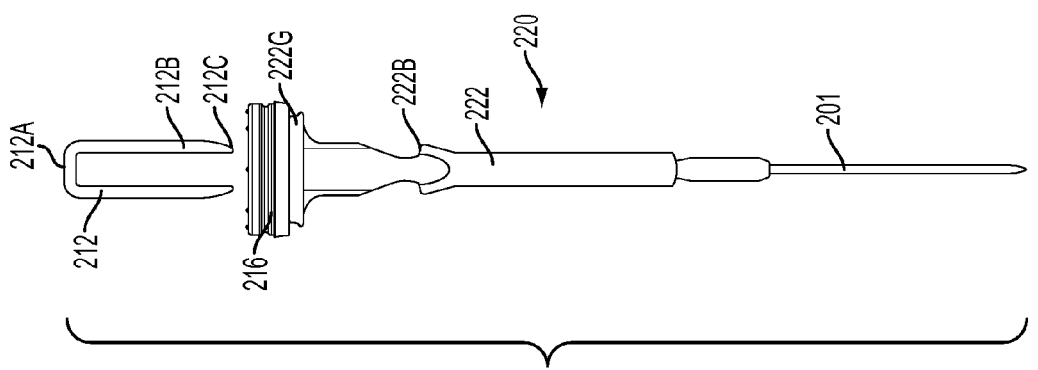
FIG. 16B is an enlarged assembled view of the needle subassembly component shown in FIG. 16A and the actuator subassembly component.
Figure 16A:
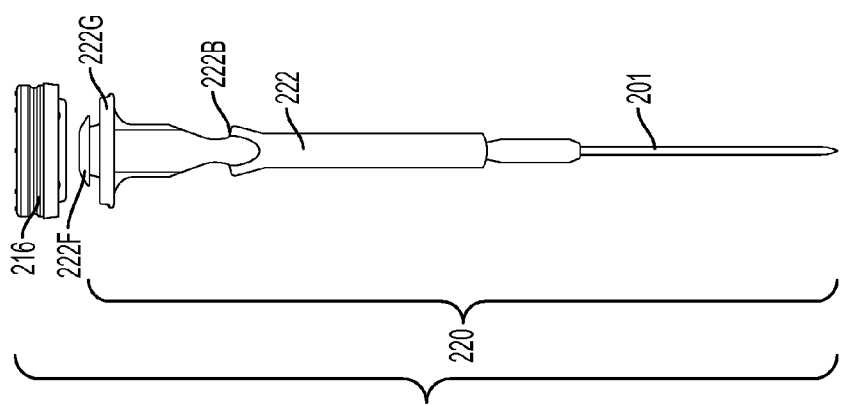
FIG. 16A is an enlarged exploded view of the needle subassembly component of the barrel adapter according to the embodiment of FIG. 11.

As may best be seen in FIG. 16A, the needle subassembly 220 includes a needle 201 and a needle-over-mold (NOM) 222. The actuator subassembly 210 includes a needle seal 216, and a push bar 212. The needle subassembly 220 is engaged with the needle seal 216 with a proximal end of the needle 201 extending through an opening 216A in the needle seal 216. The NOM 222 may be securely coupled to the needle seal 216 in any appropriate manner. For example, in the illustrated embodiment, the NOM 222 includes a plurality of flanges, a first of such flanges 222F engaging an internal flange 216C of the needle seal 216, and a second of said flanges 222G being disposed along a lower surface of the needle seal 216. Further features of the NOM will be described below with regard to the relationship of the needle refraction subassembly 260 and the actuator subassembly 210.

The push bar 212 of the actuator subassembly 210 may best be seen in FIG. 16B. The push bar 212 includes a proximal contact surface 212A and at least one depending force transfer element 212B. Here, a pair of force transfer elements 212B extends through throughways in the needle seal 216. In assembly, the proximal contact surface 212A is disposed proximal the needle seal 216, as shown in FIG. 16B. In contrast to the first embodiment, however, the force transfer element 212B of the push bar 212 includes actuating surfaces 212C, here, angled surfaces. In other words, this embodiment does not include a separate actuator. Rather, the push bar 212 and actuator are a unitary component.

While the push bars 112, 212 of the embodiments of the actuator subassemblies 110, 210 of FIGS. 1-20 have generally an inverted U-shape presenting a relatively flattened elongated proximal contact surface 112A, 212A and a pair of depending force transmitting elements 112B, 212B, it will be appreciated by those of skill in the art that the push bar may have an alternate design. As illustrated, for example, in the embodiment of the actuator subassembly 310 of FIGS. 21A-21B, the push bar 312 includes a circular proximal contact surface 312A with a pair of depending force transmitting element 312B extending through a needle seal 316. In some embodiments of the invention, such a circular proximal contact surface 312A provides a larger proximal contact surface 312A for contact by a plunger seal (not illustrated) during operation. In this embodiment, the circular proximal contact surface 312A includes a central opening 312C therethrough.

Further, while the push bars 112, 212, 312 of the embodiments of FIGS. 1-21B include a pair of depending force transmitting elements 112B, 212B, 312B, a greater or lesser number of force transmitting elements may be provided, that is, it may include a single force transmitting element or three or more force transmitting elements. For example, the push bar may include a single force transmitting element. In the actuator subassembly 410 of FIGS. 22A-22B, for example, the push bar 412 includes a generally circularly shaped proximal contact surface 412A with three such depending force transmitting elements 412B extending through needle seal 416. In some embodiments, the inclusion of three or more such force transmitting element 412B may enhance the force distribution from the plunger seal (not shown) for actuation of the associated needle retraction mechanism (not shown).

Figure 21A:
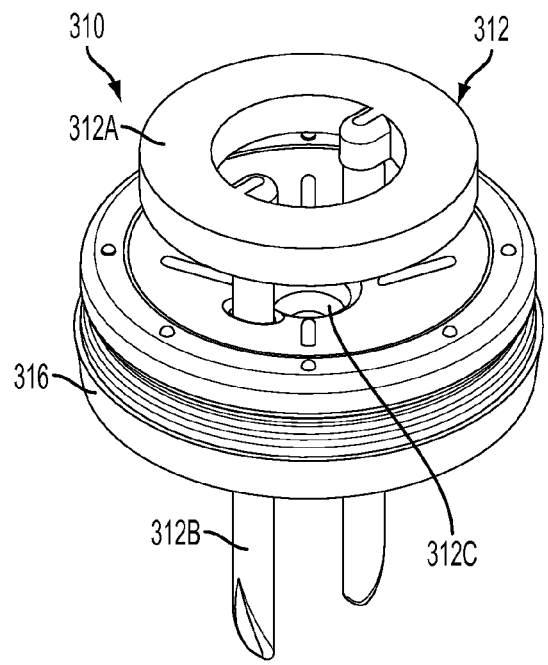
FIG. 21A is an enlarged, isometric view of an alternate embodiment of an actuator subassembly according to teachings of the present invention.
Figure 21B:
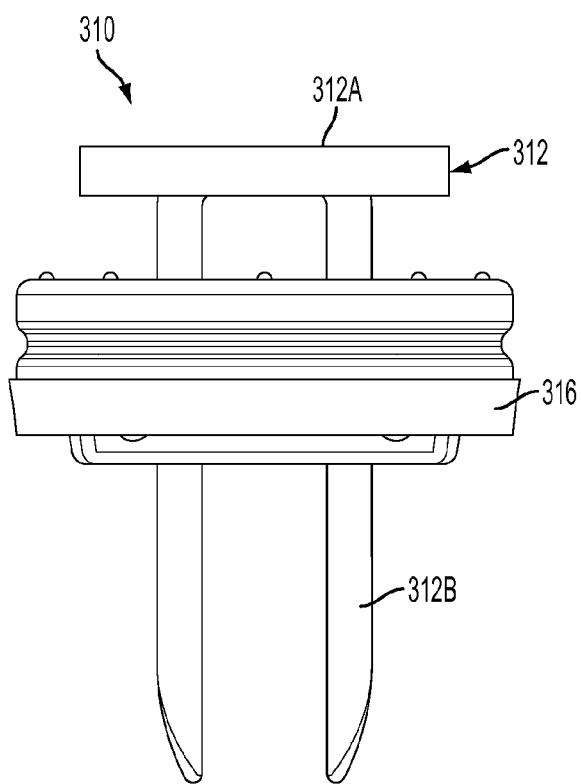
FIG. 21B is a side view of the actuator subassembly of FIG. 21A.
Figure 22A:
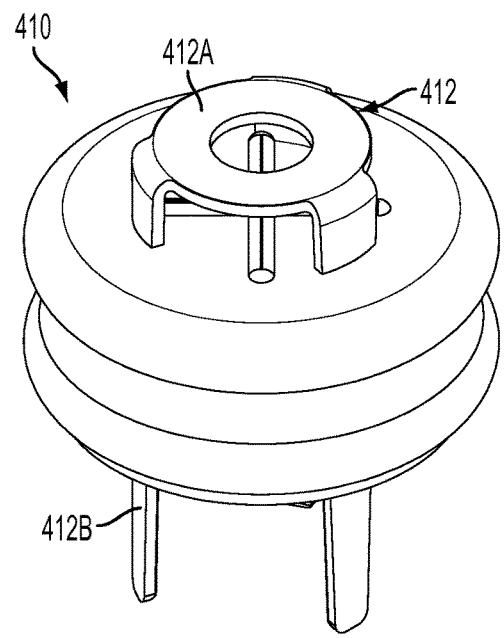
FIG. 22A is an enlarged, isometric view of an alternate embodiment of an actuator subassembly according to teachings of the present invention.
Figure 22B:
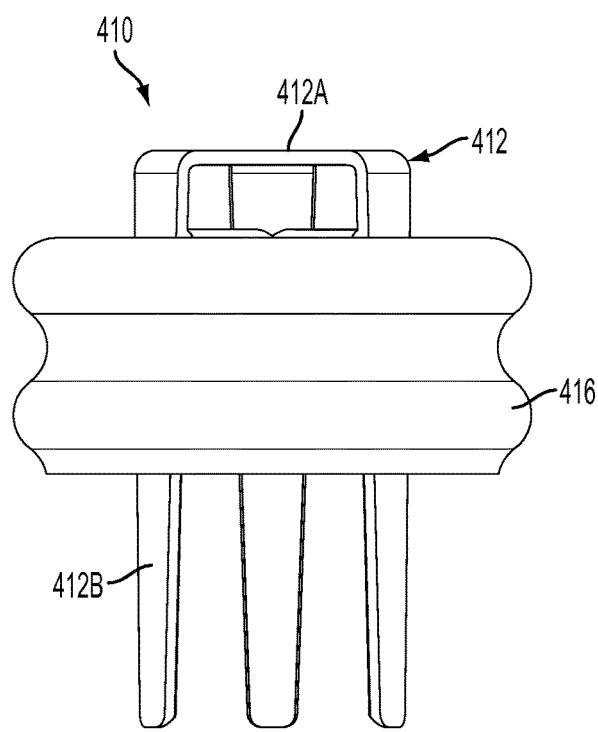
FIG. 22B is a side view of the actuator subassembly of FIG. 22A.

It will likewise be noted from the embodiments of FIGS. 21A-22B that the force transmitting elements may be of any appropriate shape. In the embodiment of FIGS. 21A-21B, the force transmitting elements 312B have a generally round cross-section, while the force transmitting elements 412B of FIGS. 22A-22B have a generally rectangular cross-section. The push bar may be fabricated by any suitable method. It will be appreciated that the push bar 412 may have certain advantages in that it may be readily fabricated using known stamping processes in which the part is cut and bent into the final shape.

Figure 17C:
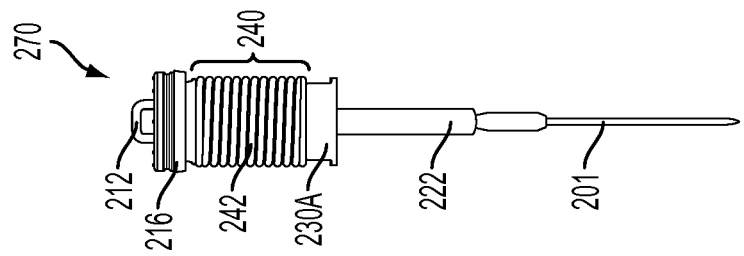
FIG. 17C is an enlarged assembled view of the needle retraction subassembly, needle subassembly and actuator subassembly of FIGS. 16A-17B.
Figure 17B:
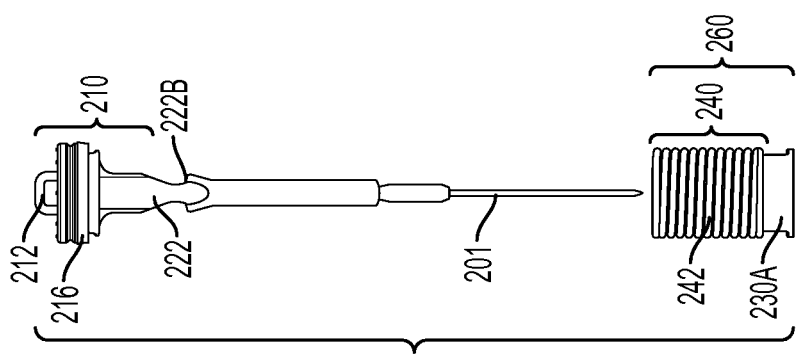
FIG. 17B is an enlarged exploded view of the assembled needle retraction subassembly of FIG. 17A and the assembled needle subassembly and actuator subassembly component of FIG. 16C.
Figure 17A:
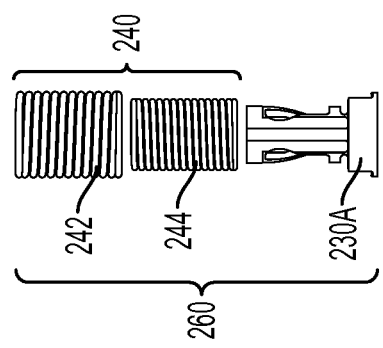
FIG. 17A is an enlarged exploded view of a needle retraction mechanism subassembly according to the embodiment of FIG. 11.

Returning now to the embodiments of FIGS. 11-19B, the needle retraction subassembly 260 is shown in greater detail in FIG. 17A, and its relationship to the remaining components of the barrel adapter 200 in FIGS. 14A and 14B. The needle retraction subassembly 260 includes at least one biasing member 240 and an actuable locking arrangement. In this embodiment, the biasing member 240 includes a pair of springs 242, 244. While the springs 242, 244 are disposed in parallel and the support structure is such that they move toward a deenergized position simultaneously, the springs 242, 244 could alternately be disposed and supported such that they move toward a deenergized position in series. Whether disposed in series or in parallel, the inclusion of two or more springs may provide certain advantages in reducing the size of the overall package of the barrel adapter 200. It will be appreciated, however, that supporting the springs in parallel 242, 244 may further enhance these advantages.

In this embodiment, the barrel tip 230 includes multiple components. That is, the spring guide 230A is formed separately from the tip portion 230D, the spring guide 230A and the tip portion 230D being coupled together during assembly. The biasing members 240, or springs 242, 244, may be received around the spring guide 230A. Inserting the assembly of the needle subassembly 220 and the actuator subassembly 210 into the spring guide 230A, the needle subassembly 220 and the spring guide 230A may be coupled together to retain the biasing members 240 in an energized position between engagement surface 230C and ledge 222C. In contrast to the first embodiment, in this embodiment, the spring guide 230A includes at least one locking prong 230B, here, a pair of locking prongs 230B, and the NOM 222 includes a locking ledge 222B, as may best be seen in FIG. 14B. An assembly 270 of the needle subassembly 220, actuator subassembly 210, and needle retraction subassembly 260 is illustrated in FIG. 17C.

It will thus be appreciated that when the push bar 212 is contacted by the plunger seal 14 at the end of administration of medication, the actuating surfaces 212C of the push bar 212 push the locking prongs 230B of the spring guide 230A outward, disengaging them from the locking ledge 222B of the NOM 222. As a result, the biasing members 240 are permitted to release energy to retract the needle subassembly 220 into the barrel 20.

The assembly 270 may be further assembled with the tip portion 230D to form the barrel adapter 200 by any appropriate mechanism. For example, in the illustrated embodiment, the tip portion 230D and the spring guide 230A may each include one or more respective engaging flange surfaces 230E (see FIG. 14B). In order to ensure proper disposition of the components, stops and mating structures may be provided along one or more of the components. In this embodiment, the NOM 222 may include at least one stop 222H, and the tip portion 230D at least one arm 230F. In assembly, the tip portion 230D may be slid axially along the NOM 222 until a position wherein the arms 230F engage the stops 222H, at which position, the flange surfaces 230E of the tip portion 230D engage the flange surfaces 230E of the spring guide 230A to couple the components together for form the barrel tip 230 shown in FIGS. 13-14B.

Additional stops may be provided for additional functionality. For example, the NOM 222 may include a second stop 222I. Upon retraction of the needle subassembly 220 into the barrel tip 230, the arms 230F of the tip portion 230D may slide along the NOM 222. Once the arms 230F pass the second stop 222I, however, the arms 230F engage the second stop 222I to prevent the needle subassembly 220 from again moving in a distal direction, effectively acting as a needle blocking mechanism, locking the needle subassembly 220 in the retracted position.

As with the first embodiment, the barrel adapter 200 may be readily assembled to a syringe 10 either prior to filling or just prior to use, and any appropriate coupling mechanism may be provided, as explained in greater detail above. Returning to FIGS. 16A-16C, the needle subassembly 220 may be assembled with the needle seal 216 by assembling the flange 222F into the needle seal 216 until such position that that flange 222F engages the flange 216C and the flange 222G engages the lower surface of the needle seal 216. As shown in FIG. 16B, the push bar 212 is then assembled into the needle seal 216 to yield the assembly shown in FIG. 16C.

Turning to FIGS. 17A-C, the needle retraction subassembly 260 may be assembled by axially assembling the springs 242, 244 to the spring guide 230A. As illustrated in FIG. 17B, the needle subassembly 220 and actuator subassembly 210 of FIG. 16C may then be assembled into the needle retraction subassembly 260 to yield the assembly 270 of FIG. 17C. The assembly 270 of FIG. 17C may then be assembled axially to the barrel tip 230 as explained above to yield the assembly illustrated in FIGS. 13-14B.

Figure 18D:
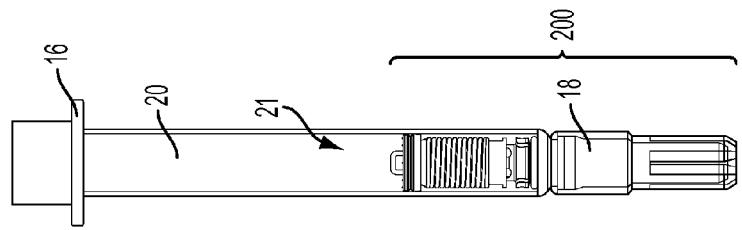
FIGS. 18C-18D show any assembly process to form an assembled safety syringe of FIG. 11.
Figure 18C:
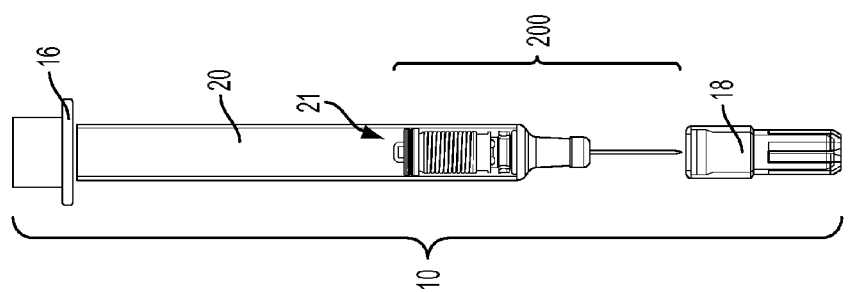
Figure 18B:
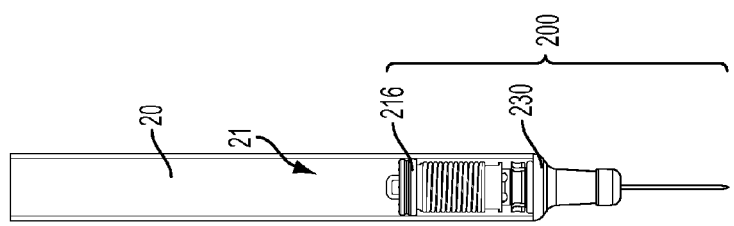
FIGS. 18A-18B show an assembly process of needle retraction subassembly, needle subassembly and actuator subassembly of FIG. 17C with barrel tip to a barrel to form a barrel adapter.
Figure 18A:
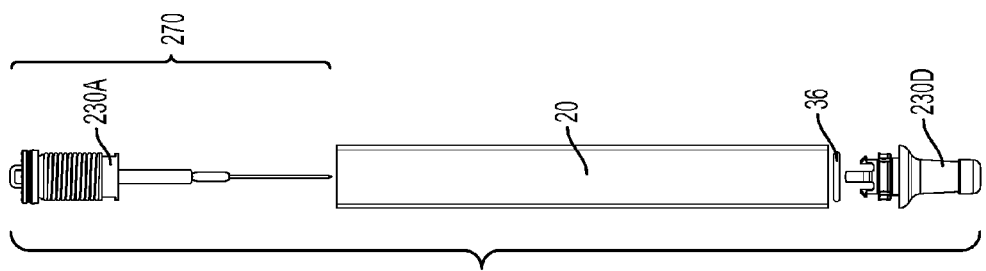
Figure 19A:
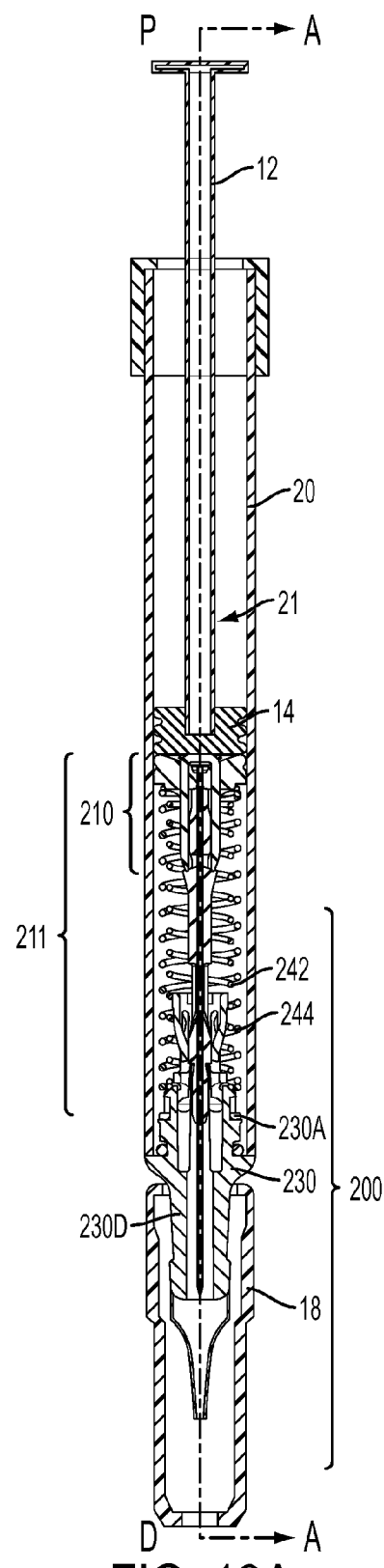
FIG. 19A is a cross-sectional view of a syringe similar to FIG. 12A, during the retraction process.
Figure 19B:
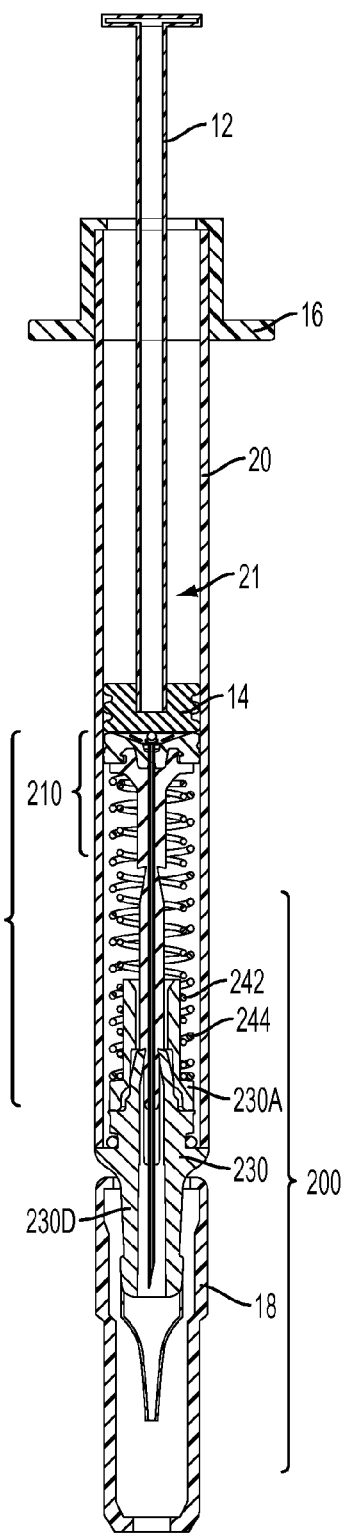
FIG. 19B is a cross-sectional view of the syringe of FIG. 19A taken at 90 degrees to the view of FIG. 19A.

Alternately, the assembly 270 of FIG. 17C may be assembled axially into a barrel 20 with the tip portion 230D, as illustrated in FIG. 18A, to yield the assembly of FIG. 18B. An O-ring 36 or the like may be provided to enhance sealing between the components. The plunger assembly 8 may be assembled into the barrel 20, and a syringe cap or needle shield 18 to the distal end of the syringe 10.

Figure 11:
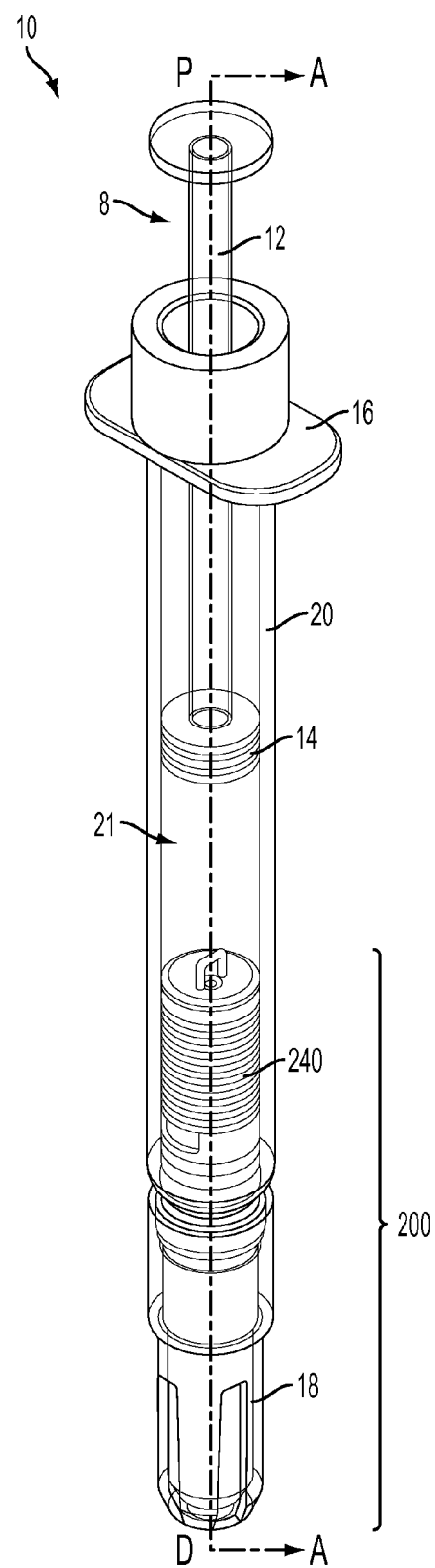
FIG. 11 is an isometric view of another embodiment of a safety syringe according to teachings of the present invention.
Figure 12A:
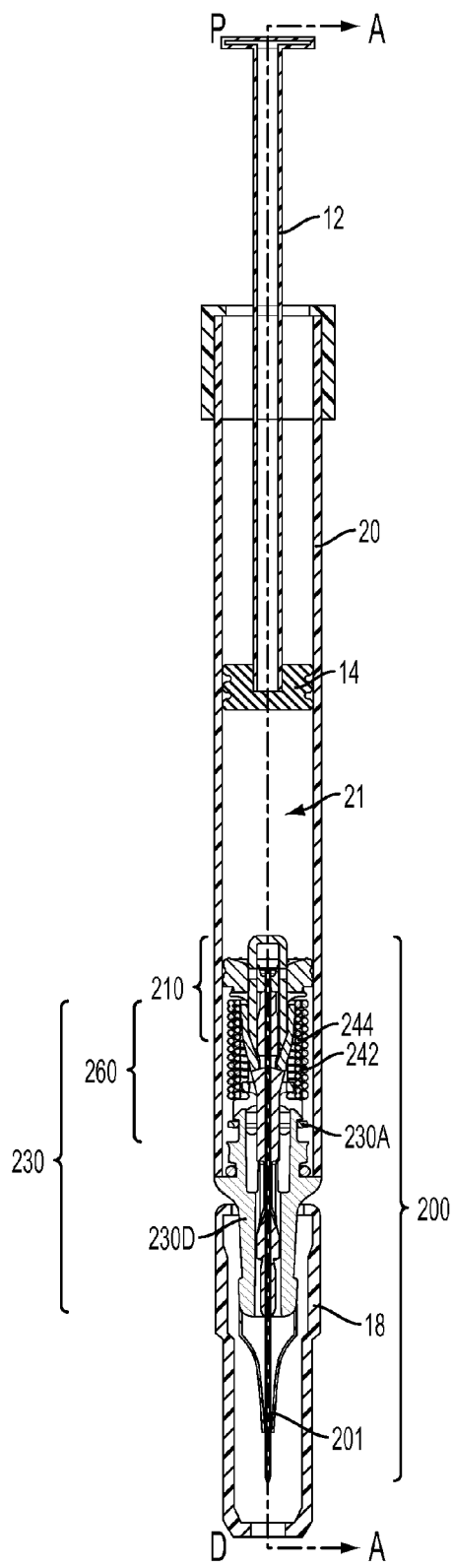
FIG. 12A is a cross-sectional view taken along line A-A of the embodiment shown in FIG. 11.
Figure 12B:
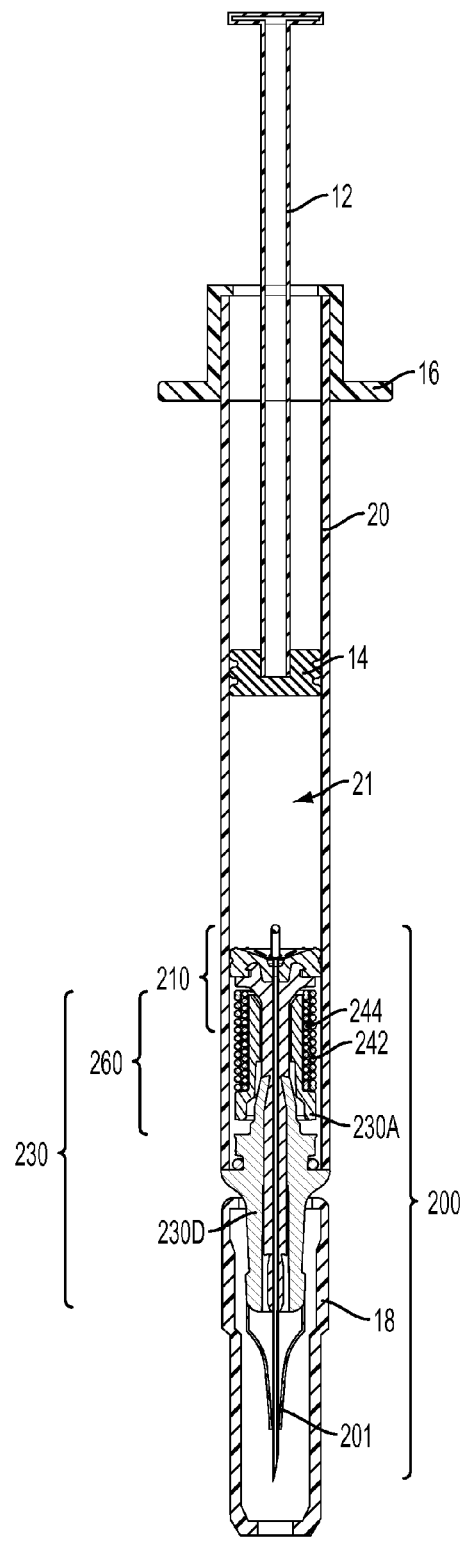
FIG. 12B is a 90 degree rotated cross-sectional view taken along line A-A in FIG. 12A.
Figure 20:
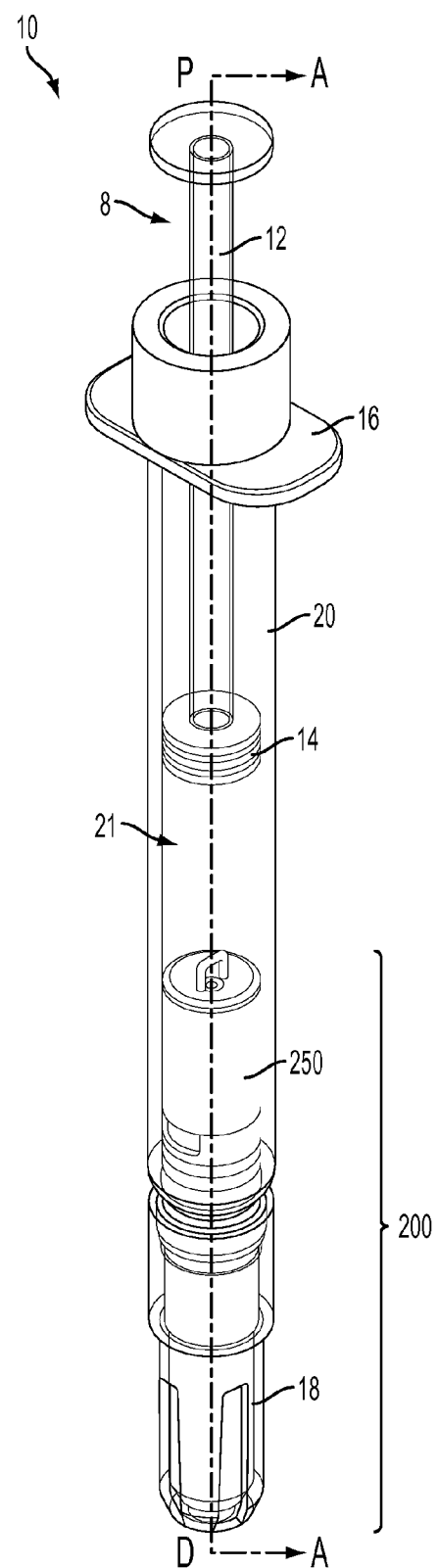
FIG. 20 is an isometric view of another embodiment of a safety syringe according to teachings of the present invention.

It will be noted that the barrel adapter 200 (as shown in FIGS. 12-14B) or syringe 10 as shown in FIG. 11 may additionally include a sleeve 250 disposed to shield the biasing member 240 from view, as shown, for example, in FIG. 20. The sleeve 250 may be disposed between the inside wall of the barrel 20 and the biasing member(s) 240. Alternately, the sleeve may be in the form of label or the like disposed about the outer surface of the barrel 20, again, concealing biasing member 240 from view. Such a product label may additionally contain, for example, instructions for use, or branding or drug information. It will be appreciated, however, that when such a sleeve 250 is disposed about the barrel adapter 200, such as in the embodiment as illustrated in FIG. 3, the sleeve 250 may additionally simplify handling of the adapter 200 during the assembly process.

Some embodiments of the present invention may provide advantages in fabrication, storage, and usage. Some embodiments of the present invention may provide configurations which allow the use of standard, commercially-available components, thereby reducing overall manufacturing costs, streamlining assembly processes, and avoiding regulatory concerns often associated with non-standard materials and components. For example, the barrel may be made of certain plastics, glass, or any other material commonly used for medical grade products. One or more components of the present invention may also be made up of certain plastics, such as the polycarbonate plastics like, for example, polycarbonate (PC), polycarbonate/acrylonitrile butadiene styrene (PC/ABS), and/or those sold under the trade name "LEXAN" by SABIC Innovative Plastics of Pittsfield, Mass. Similarly, certain elastomeric polymers or rubbers may be utilized, such as the rubber products sold under the trade name "HELVOET" by Datwyler Pharma Packaging USA Inc. of Pennsauken, N.J., for components such as the needle seal 116, 216 and the plunger seal 14. Various medical grade metals, such as stainless steel, may be utilized for the needle 101, 201, as would be appreciated by an ordinarily skilled artisan. These components, the barrel adapters 100, 200, and the safety syringes 10 may be shaped or sized in a myriad of different configurations to meet the desired parameters. These components, barrel adapters 100, 200, and syringes 10 may be assembled, and/or filled with a drug, by a multitude of processes known in the art. For example, well known glues or welding methods such as ultrasonic welding may be employed to assemble the components of the present invention.

The novel barrel adapter and syringe designs of the present invention enable relatively simplified assembly and filling processes. One method for assembling a safety syringe having a barrel adapter 100, 200, a plunger assembly 8 having a plunger rod 12 and plunger seal 14, and a barrel 20 having a longitudinal axis includes the steps of: assembling the barrel adapter 100, 200; mounting the barrel tip 130, 230 to a distal end of the barrel 20; and mounting the plunger assembly having a plunger seal 14 and a plunger rod 12 to a proximal end of the barrel 20. The barrel adapter 100, 200 may be fixedly mounted, such as by glue, to the distal end of the barrel 20. The plunger assembly 8 may be movably mounted to the distal end of the barrel 20 by first inserting the plunger seal 14 into the barrel 20 and then inserting the plunger rod 12 into the plunger seal 14 by screw connection or another known method of connection. The method for assembling the safety syringe may further include the step of filling the barrel 20 with a drug, after the step of mounting the barrel tip 130, 230 but prior to the step of mounting the plunger assembly.

The plunger seal 14 may comprise of an elastomeric material and be sized such that it provides a compression fit with an inner diameter of the barrel 20 in order to maintain the sterility and container integrity of the drug chamber. The plunger seal 14 may also include an aperture, such as an axial pass-through, for example to enable removal of air from the drug chamber as the plunger seal 14 is depressed into position within the barrel 20. Accordingly, the drug may be filled into the barrel 20 prior to mounting of the plunger assembly 8, or just prior to mounting of the plunger seal 14. In the latter configuration, the plunger seal 14 may be slide into position in contact with the drug fluid in a sterile environment or other aseptic conditions. The plunger seal 14 aperture allows for residual air bubbles, if any, to escape the drug chamber when the plunger seal 14 is pushed into contact with the fluid. Subsequently, the plunger seal aperture may be closed or capped by connection with the plunger rod 12, which may be screwed into the plunger seal aperture. The syringe, which may be considered a prefilled syringe, is then ready for use. Alternatively, the components of the present invention may be assembled without the drug filling step, such as in a fill at time-of-use process. In one such process, the drug may be filled by backwards drawing the plunger rod 12 and plunger seal 14 while the needle 101, 201 is aseptically connected to a drug vial. In this manner, the drug fluid is pulled by vacuum action into the drug chamber through the needle 101, 201.

In at least one embodiment, the barrel adapter 100, 200 is in a compressed configuration prior to mounting into the barrel 20. For example, the biasing member 140, 240 (e.g., spring 242, 244) may be compressively engaged, such as in an energized stage, between the NOM 122, 222 and the barrel tip 130, 230 prior to mounting the barrel adapter 100, 200 into the barrel 20. In another embodiment, these components may be mounted into the barrel 20 prior to compressing and locking the biasing member 140, 240 into place. Accordingly, the method may further include the steps of compressing the biasing member 140, 240 and locking the locking arrangement into an engaged and energized position after the mounting of the barrel adapter 100, 200 to the barrel 20. It is contemplated that, in at least one embodiment, the plunger assembly 8 may be utilized in assembly of the barrel adapter 100, 200 with the barrel 20. For example, prior to filling a drug into the drug chamber, the plunger seal 14 and plunger rod 12 may be used to push the needle subassembly 120, 220 and actuator subassembly 110, 210 into place substantially within the barrel tip 130, 230 and the distal end of the barrel 20 in locked engagement with the one or more corresponding locking aspects of the barrel tip 130, 230. During such assembly, the biasing member(s) 140, 240 may be disposed on the barrel tip 130, 230 or on the NOM 122, 222 such that it is energized as the needle subassembly 120, 220 and actuator subassembly 110, 210 are moved into place substantially within the barrel tip 130, 230. Alternately, in the case of the second embodiment, the plunger seal 14 and plunger rod 12 may be utilized to push the assembly 270 into position in the barrel 20 and into locking engagement with the tip portion 230D. The plunger rod 12, and optionally plunger seal 14, may then be removed from the barrel 20 to facilitate the filling process, as may be the case for a prefilled syringe filling process. Alternatively the plunger rod 12 and plunger seal 14 may remain in place to later be drawn backwards, as may be the case for a fill at time-of-use filling process. The barrel adapters 100, 200 and safety syringes 10 described herein are configured such that they may readily be manufactured individually, or in a group, as is the case in a tray-based manufacturing and filling process.

The safety syringes of the present invention are configured to be used in a manner similar to conventional syringes. The method of use includes the steps: depressing the plunger assembly to facilitate delivery of a drug from the barrel 20; upon completion of the drug delivery, triggering the locking arrangement to release the at least one biasing member from its energized state; and, by contact between the biasing member and the needle subassembly 120, 220, causing the needle subassembly 120, 220 and/or the needle 101, 201 to retract into the barrel 20.

Regardless of the particular components, the methods of use for the safety syringes of the present invention are relatively similar. By releasing the locking arrangement from its engaged condition, the biasing member 140, 240 is allowed to expand causing the needle subassembly 120, 220 and/or needle 101, 201 to retract in the proximal direction substantially along a longitudinal axis of the barrel 20. In some embodiments of the present invention, the entire needle subassembly 120, 220 is caused to retract, while in other embodiments only certain components thereof, including the needle 101, 201, are caused to retract upon release of the locking arrangement and activation of the biasing member 140, 240. Optionally, the method of use may include the step of blocking the needle 101 from axially translating in the distal direction after the needle 101, 201 has retracted into the barrel 20, such as, by way of example only, clip arms 124A of a clip 124 or elements such as arms 230F of the barrel tip 230 or the like.

The present invention provides component assemblies, such as barrel adapters, which provide needle retraction, syringes which integrate such safety mechanisms, methods of manufacturing such adapters and safety syringes, and their methods of use. As stated above, the barrel adapters and safety syringes may be utilized in a number of different configurations. For example, as stated above, the novel barrel adapters of the present invention are configured to mate with, be mounted in, or otherwise connect to a barrel, however it may be desirable to pre-form any of the components of the barrel adapter to the barrel. Such modifications are contemplated by and encompassed in the embodiments of the present invention. Similarly, the barrel adapter may contain a needle hub and needle seal, which may be separate components or a dual-purpose single component. Other components may similarly be single components, unified components, or multi-purpose components, as described in the embodiments discussed above. Furthermore, there are a number of different configurations which may utilize the novel needle retraction mechanisms described herein, which may generally be contained substantially within the barrel tip and the distal end of the barrel. Accordingly, similar to the examples provided above, the barrel adapters and safety syringes of the present invention may be configured, modified, and utilized to initiate drug delivery and activate needle refraction in any number of configurations while remaining within the breadth and scope of the present invention. Thus, it is intended that the present invention covers the modifications and variations of this invention provided they come within the scope of the appended claims and their equivalents.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A method of assembling a barrel adapter for a safety syringe, the method comprising the steps of
   assembling a push bar to a needle seal with at least a contact surface of the push bar disposed proximal to the needle seal and with at least one force transfer element extending through the needle seal,
   coupling a needle subassembly including a needle to the needle seal with a proximal end of the needle providing a fluid pathway through the needle seal,
   disposing the needle subassembly at least partially within a barrel tip, energizing at least one biasing member between a needle-over-mold of the needle subassembly and a spring guide of the barrel tip, and coupling the needle subassembly to the barrel tip with an actuable locking arrangement to maintain the at least one biasing member in an energized state, the actuable locking arrangement being disposed to maintain the at least one biasing member in an energized position when the locking arrangement is locked and release the at least one biasing member when actuated, the at least one biasing member being disposed to move the needle from an injection position to a retracted position when the at least one biasing member is released from the energized position, the locking arrangement being actuable by axial movement of an actuating surface relative to the actuable locking arrangement, the actuable locking arrangement being actuable by axial movement of the push bar, the at least one force transfer element, and the actuating surface as a result of contact and depression of a plunger assembly to actuate the actuable locking arrangement to at least partially release the at least one biasing member from the energized state and retract the needle at least partially inside of at least one of the barrel tip and the barrel.

2. The method of claim 1 wherein the step of assembling a push bar to a needle seal includes assembling the at least one force transfer element through the needle seal, and disposing an actuator including the at least one actuating surface distally the needle seal.

3. The method of claim 1 further including disposing a needle blocking mechanism in a position adapted to block axial movement of the needle in a distal direction following retraction.

4. The method of claim 1 wherein the step of coupling the needle subassembly to the barrel tip with an actuable locking arrangement includes disposing at least one locking prong to engage a locking ledge.

5. The method of claim 1 further including coupling the spring guide and a tip portion forming the distal end of the barrel tip to form the barrel tip.

6. The method of claim 1 further including disposing a sleeve about the at least one biasing member.

7. A method of assembling an automatically retractable safety syringe including the steps of claim 1, and further including sealingly engaging the barrel tip with a distal end of a syringe barrel, and assembling a plunger assembly for axial movement within the barrel by assembling a plunger seal through a proximal end of the barrel.

8. The method of claim 7 further including disposing a subassembly including the at least one biasing member energized between the needle-over-mold of the needle subassembly and a spring guide of the barrel tip within the distal end of the syringe barrel, and coupling a tip portion forming the distal end of the barrel tip to the spring guide and the distal end of the barrel.

9. The method of claim 1 wherein the step of assembling the push bar to the needle seal includes disposing the at least one force transfer element for axial translation through the needle seal.

10. The method of claim 9 wherein the step of assembling the push bar to the needle seal includes disposing the at least one force transfer element such that axial translation of the at least one force transfer element moves an actuating surface in an axial direction.

* * * * *